(12) United States Patent
Bissantz et al.

(10) Patent No.: US 7,351,706 B2
(45) Date of Patent: Apr. 1, 2008

(54) INDOL-3-YL-CARBONYL-SPIRO-PIPERIDINE DERIVATIVES

(75) Inventors: Caterina Bissantz, Village-Neuf (FR); Christophe Grundschober, Rodersdorf (CH); Hasane Ratni, Habsheim (FR); Mark Rogers-Evans, Oberwil BL (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/640,739

(22) Filed: Dec. 18, 2006

(65) Prior Publication Data
US 2007/0155761 A1    Jul. 5, 2007

(30) Foreign Application Priority Data
Jan. 5, 2006    (EP)    .................................. 06100118

(51) Int. Cl.
*A61K 31/537*    (2006.01)
*A61K 31/438*    (2006.01)
*C07D 413/14*    (2006.01)
*C07D 401/14*    (2006.01)

(52) U.S. Cl. ........................ 514/230.5; 544/71; 546/18; 546/17; 514/278

(58) Field of Classification Search ............. 514/230.5, 514/278; 544/71; 546/18, 17
See application file for complete search history.

(56) References Cited

U.S. PATENT DOCUMENTS

| 6,013,652 | A | 1/2000 | Maccoss et al. |
| 2001/0039286 | A1 | 11/2001 | Dinnell et al. |
| 2004/0067939 | A1 | 4/2004 | Corbett et al. |

FOREIGN PATENT DOCUMENTS

| WO | WO 99/09984 | 3/1999 |
| WO | WO 01/22919 | 4/2001 |
| WO | WO 2007/006688 A1 | 1/2007 |

OTHER PUBLICATIONS

Ebner, et al., Eur. J. Neurosci. vol. 15(2), pp. 384-388 (2002).
Liebsch et al., Regul. Pept. vol. 59(2) pp. 229-239 (1995).
Michelini et al., Ann NY Acad Sci vol. 897, pp. 198-211 (1999).
Van Kerckhoven et al., Eur. J. Pharmacol. vol. 449 (1-2) pp. 135-141 (2002).
Swain et al., J. Med. Chem. (1991) vol. 34 p. 140-151.
Clark et al., J. Med. Chem. (1983) vol. 26(5) p. 657-661.
Sohda et al., J. Med. Chem. (1992) vol. 35(14) p. 2617-2626.
Perregaard, J., et al., Journal of Medicinal Chemistry, (1995), vol. 38, No. 11, p. 1998-2008, XP000941460.
Xiang, M.A., et al., Bioorganic & Medicinal Chemistry Letters, (2004), vol. 14, No. 11, p. 2987-2989, XP004841329.

*Primary Examiner*—Charanjit S. Aulakh
(74) *Attorney, Agent, or Firm*—George W. Johnston; Patricia S. Rocha-Tramaloni; Kimberly J. Prior

(57) ABSTRACT

This invention relates to indol-3-yl-carbonyl-spiro-piperidine derivatives which act as V1a receptor antagonists and which are represented by Formula I:

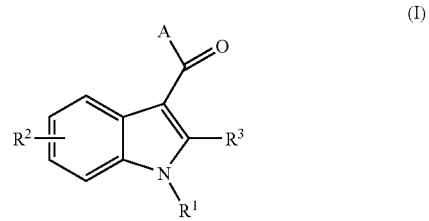

wherein the spiropiperidine-head group A and the residues $R^1$, $R^2$ and $R^3$ are as defined herein. The invention further relates to pharmaceutical compositions containing such compounds, their use in the treatment of dysmenorrhea, hypertension, chronic heart failure, inappropriate secretion of vasopressin, liver cirrhosis, nephrotic syndrome, obsessive compulsive disorder, anxiety and depressive disorders, and to methods of preparation thereof.

21 Claims, No Drawings

INDOL-3-YL-CARBONYL-SPIRO-PIPERIDINE DERIVATIVES

PRIORITY TO RELATED APPLICATIONS

This application claims the benefit of European Application No. 06100118.6, filed Jan. 5, 2006, which is hereby incorporated by reference in its entirety.

BACKGROUND OF THE INVENTION

Vasopressin is a 9 amino acid peptide mainly produced by the paraventricular nucleus of the hypothalamus. Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water excretion and mediates the antidiuretic effects of vasopressin.

In the periphery vasopressin acts as a neurohormone and stimulates vasoconstriction, glycogenolysis and antidiuresis. In the brain vasopressin acts as a neuromodulator and is elevated in the amygdala during stress (Ebner, K., C. T. Wotjak, et al. (2002). "Forced swimming triggers vasopressin release within the amygdala to modulate stress-coping strategies in rats." *Eur J Neurosci* 15(2): 384-8). The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky, I. F., S. B. Hu, et al. (2003). "Profound Impairment in Social Recognition and Reduction in Anxiety-Like Behavior in Vasopressin V1a Receptor Knockout Mice." *Neuropsychopharmacology*). The down-regulation of the V1a receptor using antisense oligonucleotide injection in the septum also causes a reduction in anxious behavior (Landgraf, R., R. Gerstberger, et al. (1995). "V1 vasopressin receptor antisense oligodeoxynucleotide into septum reduces vasopressin binding, social discrimination abilities, and anxiety-related behavior in rats." *Regul Pept* 59(2): 229-39).

The V1a receptor is also mediating the cardiovascular effects of vasopressin in the brain by centrally regulating blood pressure and heart rate in the solitary tract nucleus (Michelini, L. C. and M. Morris (1999). "Endogenous vasopressin modulates the cardiovascular responses to exercise." *Ann N Y Acad Sci* 897: 198-211). In the periphery it induces the contraction of vascular smooth muscles and chronic inhibition of the V1a receptor improves hemodynamic parameters in myocardial infarcted rats (Van Kerckhoven, R., I. Lankhuizen, et al. (2002). "Chronic vasopressin V(1A) but not V(2) receptor antagonism prevents heart failure in chronically infarcted rats." *Eur J Pharmacol* 449(1-2): 135-41).

Thus vasopressin receptor antagonists are useful as therapeutics in the conditions of dysmenorrhea, hypertension, chronic heart failure, inappropriate secretion of vasopressin, liver cirrhosis, nephrotic syndrome, obsessive compulsive disorder, anxiety and depressive disorders.

SUMMARY OF THE INVENTION

The present invention provides compounds of formula (I):

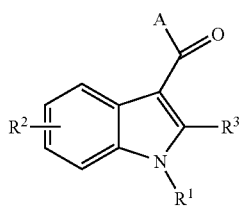

(I)

wherein

A is selected from the following groups (a), (b), (c), (d), (e) and (f):

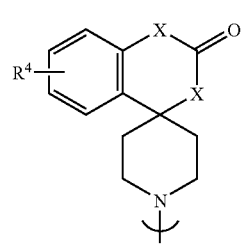

(a)

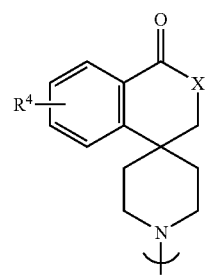

(b)

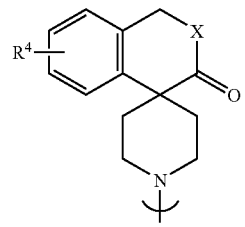

(c)

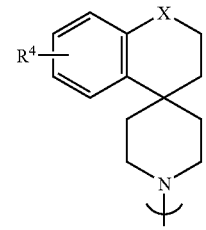

(d)

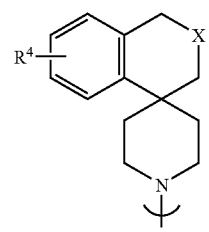

(e)

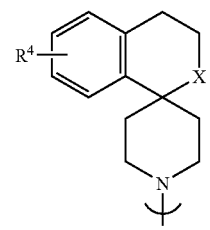

(f)

each X is the same or different and is $CR^{iii}R^{iv}$, $NR^{iii}$ or O, wherein in (a), only one X can be O, the other being $CR^{iii}R^{iv}$ or $NR^{iii}$;

$R^1$ is H,
  $C_{1-6}$-alkyl optionally substituted by CN,
  aryl, 5 or 6 membered heteroaryl or sulfonylaryl each of which is optionally substituted by one or more B,
  —$(CH_2)_m$—$R^a$ wherein $R^a$ is:
    $OR^i$,
    $NR^iR^{ii}$, or
    $C_{3-6}$-cycloalkyl, 4 to 7 membered-heterocycloalkyl, aryl, or 5 or 6 membered heteroaryl eaqch of which is optionally substituted by one or more B,
  or —$(CH_2)_n$—(CO)—$R^b$  or  —$(CH_2)_n$—$(SO_2)$—$R^b$, wherein $R^b$ is:
    $C_{1-6}$-alkyl,
    $C_{1-6}$-alkoxy,
    $C_{3-6}$-cycloalkyl,
    —$(CH_2)_m$—$NR^{iii}R^{iv}$,
    $NR^iR^{ii}$, or
    $C_{3-6}$-cycloalkyl, 4 to 7 membered-heterocycloalkyl, aryl, or 5 or 6 membered heteroaryl each of which is optionally substituted by one or more B, or $R^1$ and $R^3$ together with the indole ring to which they are attached form a 5 or 6 membered heterocycloalkyl which is optionally substituted by (CO);

there can be one or more $R^2$ wherein each
$R^2$ is independently H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, benzyloxy, or $C_{1-6}$-haloalkyl,
  or two $R^2$ together with the indole ring to which they are attached form an oxo or dioxo bridge;

$R^3$ is H,
  halo,
  —(CO)—$R^c$, wherein $R^c$ is:
    $C_{1-6}$-alkyl,
    —$(CH_2)_n$—$NR^iR^{ii}$,
    —$(CH_2)_n$—$NR^{iii}R^{iv}$, or
    5 or 6 membered heterocycloalkyl optionally substituted by $C_{1-6}$-alkyl,
  or $C_{1-6}$-alkyl or aryl, each of which is optionally substituted by halo,
    —O(CO)—$C_{1-6}$-alkyl, or
    —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

there can be one or more $R^4$ wherein each
$R^4$ is independently H, halo, $C_{1-6}$ alkyl, $C_{1-6}$ alkoxy, or CN, or two $R^4$ together with the phenyl ring to which they are attached form an oxo or dioxo bridge;

B is halo,
  CN,
  $NR^iR^{ii}$,
  $C_{1-6}$-alkyl optionally substituted by CN, halo or $C_{1-6}$-alkoxy,
  $C_{1-6}$-alkoxy,
  $C_{1-6}$-haloalkoxy,
  $C_{3-6}$-cycloalkyl,
  —C(O)O—$C_{1-6}$-alkyl,
  —C(O) $NR^iR^{ii}$,
  —C(O)—$C_{1-6}$-alkyl,
  —$S(O)_2$—$C_{1-6}$-alkyl,
  —$S(O)_2$—$NR^iR^{ii}$,
  $(CR^{iii}R^{iv})$-phenyl, or
  $(CR^{iii}R^{iv})_n$-5 or 6 membered heteroaryl, wherein the phenyl or 5 or 6 membered heteroaryl moiety is optionally substituted by one or more substituent(s) selected from the group consisting of:
    halo, CN, $NR^iR^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—$NR^iR^{ii}$, —C(O)-$C_{1-6}$-alkyl, —$S(O)_2$—$C_{1-6}$-alkyl, and —$S(O)_2$—$NR^iR^{ii}$;

$R^i$ and $R^{ii}$ are each independently H, $C_{1-6}$-alkyl, $C_{1-6}$-alkylene-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl or —$S(O)_2$—$NR^{iii}R^{iv}$;

$R^{iii}$ is H, $C_{1-6}$-alkyl or $C_{1-6}$-alkylene-$N(R^{iv})_2$;
$R^{iv}$ is H or $C_{1-6}$-alkyl;
m is 1 to 6;
n is 0 to 4;

and pharmaceutically acceptable salts thereof.

The compounds of formula (I) can contain some asymmetric carbon atoms. Accordingly, the present invention includes all stereoisomeric forms of the compounds of formula (I), including each of the individual enantiomers and mixtures thereof.

Compounds of formula (I) have a good activity on the V1a receptor. Therefore, the invention provides pharmaceutical compositions containing a therapeutically effective amount of a compound of the invention and a pharmaceutically acceptable carrier. The invention further provides methods for treating dysmenorrhea, hypertension, chronic heart failure, inappropriate secretion of vasopressin, liver cirrhosis, nephrotic syndrome, obsessive compulsive disorder, anxiety and depressive disorders which comprise administering to an individual a therapeutically effective amount of a compound of formula (I) or a pharmaceutically acceptable salt thereof.

The preferred indications with regard to the present invention are anxiety and depressive disorders.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "aryl" means a monovalent cyclic aromatic hydrocarbon moiety consisting of a mono-, bi- or tricyclic aromatic ring. The aryl group can be optionally substituted with one, two, three, or four substituents. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, and diphenylisopropylidenyl, as well as those specifically illustrated by the examples herein below. Substituents for aryl include, but are not limited to, halogen, $C_{1-6}$-alkyl, and $C_{1-6}$-alkoxy. Preferred aryl are phenyl and naphthyl, and still more preferably phenyl. The aryl moieties of the invention further can be ortho substituted by two substituents which together with the carbons of the aryl moiety form a fused, saturated or partially saturated, 5- to 6-membered ring containing one or two heteroatoms selected from O and N. Preferably the additional ring is a 5- to 6-membered ring containing two oxygen atoms.

Examples of such substituted aryl moieties include, but are not limited to, benzodioxanyl, dihydro-benzofuranyl, benzodioxolyl, benzopyranyl, benzoxazinyl, benzoxazinonyl, benzopiperidinyl, benzopiperazinyl, benzopyrrolidinyl, benzomorpholinyl, methylenedioxyphenyl, ethylenedioxyphenyl, as well as those specifically illustrated by the examples herein below The term "$C_{1-6}$-alkyl" denotes a saturated straight or branched hydrocarbon chain group containing from 1 to 6 carbon atoms, for example, methyl, ethyl, propyl, isopropyl, n-butyl, i-butyl, 2-butyl, t-butyl and the like. Preferred $C_{1-6}$-alkyl groups are $C_{1-4}$-groups, i.e. with 1-4 carbon atoms.

The term "$C_{1-6}$-alkoxy" denotes a group wherein the alkyl residue is as defined above, and which is attached via an oxygen atom. Preferred $C_{1-6}$-alkoxy groups are methoxy and ethoxy as well as those specifically illustrated by the examples herein below.

The term "$C_{2-6}$-alkenyl" denotes a carbon chain of 2 to 6 carbon atoms comprising a double bond in its chain. $C_{2-6}$-alkenyl groups include ethenyl, propen-1-yl, propen-2-yl, buten-1-yl, buten-3-yl, penten-1-yl, penten-2-yl, penten-3-yl, penten-4-yl, hexen-1-yl, hexen-2-yl, hexen-3-yl, hexen-4-yl and hexen-5-yl, as well as those specifically illustrated by the examples herein below.

The term "benzyloxy" denotes a benzyl group attached via an oxygen atom.

The term "halogen" or "halo" denotes chlorine (Cl), iodine (I), fluorine (F) and bromine (Br).

The term "$C_{1-6}$-haloalkyl" denotes a $C_{1-6}$-alkyl group as defined above which is substituted by one or more halogen atoms. Examples of $C_{1-6}$-haloalkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred $C_{1-6}$-haloalkyl are difluoro- or trifluoro-methyl or ethyl.

"$C_{1-6}$-haloalkoxy" denotes a $C_{1-6}$-alkoxy group as defined above which is substituted by one or more halogen atoms. Examples of $C_{1-6}$-haloalkoxy include but are not limited to methoxy or ethoxy, substituted by one or more Cl, F, Br or I atom(s) as well as those groups specifically illustrated by the examples herein below. Preferred $C_{1-6}$-haloalkoxy are difluoro- or trifluoro-methoxy or ethoxy.

The term "$C_{3-6}$-cycloalkyl" denotes a monovalent or divalent saturated carbocyclic moiety consisting of a monocyclic ring. Cycloalkyl can optionally be substituted with one, two, three or four substituents, wherein each substituent is independently hydroxy, $C_{1-6}$-alkyl, $C_{1-6}$-alkoxy, halogen, amino, unless otherwise specifically indicated. Examples of cycloalkyl moieties include optionally substituted cyclopropyl, optionally substituted cyclobutyl, optionally substituted cyclopentyl and optionally substituted cyclohexyl as well as those specifically illustrated by the examples herein below.

The term "4 to 7 membered heterocycloalkyl" is synonymous with "heterocyclyl" and means a monovalent saturated heterocyclic moiety, consisting of one ring of 4 to 7 atoms as ring members, including one, two, or three heteroatoms chosen from nitrogen, oxygen or sulfur, the rest of the ring atoms being carbon atoms. 4 to 7 membered heterocycloalkyl can optionally be substituted with one, two, three or four substituents, wherein each substituent is independently hydroxy, $C_{1-6}$-alkyl, $C_{1-6}$-alkoxy, $C_{1-6}$-thioalkyl, halo, $C_{1-6}$-haloalkyl, $C_{1-6}$-hydroxyalkyl, alkoxycarbonyl, amino, $C_{1-6}$-alkylamino, di($C_{1-6}$)alkylamino, aminocarbonyl, or carbonylamino, unless otherwise specifically indicated. Examples of heterocyclic moieties include, but are not limited to, optionally substituted oxetane, optionally substituted tetrahydro-furanyl, optionally substituted piperidinyl, optionally substituted pyrrolidinyl, optionally substituted morpholinyl, optionally substituted piperazinyl, and the like or those which are specifically exemplified herein. Substituents can be selected from $C_{1-6}$-alkyl, $C_{1-6}$-alkoxy, $C_{1-6}$-haloalkyl, halo, CN, OH, $NH_2$, as well as those substituents which are specifically illustrated in the examples hereinafter.

The term "5 or 6 membered heteroaryl" means an aromatic ring of 5 or 6 ring atoms as ring members containing one, two, or three ring heteroatoms selected from N, O, or S, the rest of the ring atoms being carbon atoms. 5 or 6 heteroaryl can optionally be substituted with one, two, three or four substituents, wherein each substituent is independently hydroxy, $C_{1-6}$-alkyl, $C_{1-6}$-alkoxy, $C_{1-6}$-thioalkyl, halo, $C_{1-6}$-haloalkyl, $C_{1-6}$-hydroxyalkyl, alkoxycarbonyl, amino, $C_{1-6}$-alkylamino, di($C_{1-6}$)alkylamino, aminocarbonyl, or carbonylamino, unless otherwise specifically indicated. Examples of heteroaryl moieties include, but are not limited to, optionally substituted imidazolyl, optionally substituted oxazolyl, optionally substituted thiazolyl, optionally substituted pyrrolyl, optionally substituted pyrazinyl, optionally substituted pyridinyl, optionally substituted pyrimidinyl, optionally substituted furanyl, and those which are specifically exemplified herein.

The term "sulfonylaryl" denotes an aryl group as defined hereinabove which is attached via a sulfonyl group.

The term "one or more" when related to $R^2$ and $R^4$ means from one to four residues which can be independently selected from the groups given below. Preferably, "one or more" in this context means one or two residues $R^2$ and $R^4$, respectively, the rest being hydrogen.

The expression "two $R^2$ together with the indole ring to which they are attached may form an oxo or dioxo bridge" denotes an oxo or dioxo bridge of the following formulae:

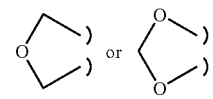

which bind two adjacent carbon atoms of the phenyl or indole ring of the compound of formula (I) to which either $R^2$ is bound.

Examples of groups illustrating the expression "$R^1$ and $R^3$ together with the indole ring to which they are attached form a 5 or 6 membered heterocycloalkyl which is optionally substituted by =O" are:

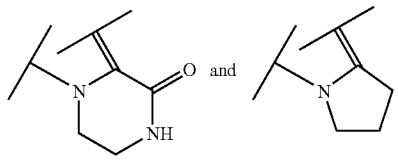

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid (addition) salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid, as well as those specifically illustrated by the examples herein below.

"Therapeutically effective amount" means an amount that is effective to prevent, alleviate or ameliorate symptoms of disease or prolong the survival of the subject being treated.

The present invention provides compounds of formula (I):

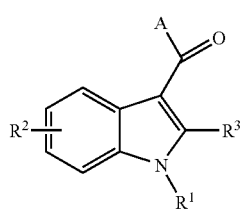
(I)

wherein

A is selected from the following groups (a), (b), (c), (d), (e) and (f):

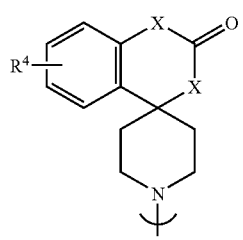
(a)

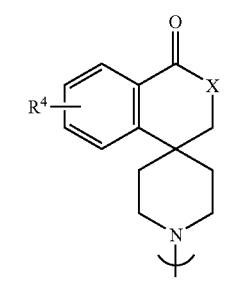
(b)

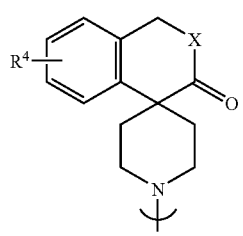
(c)

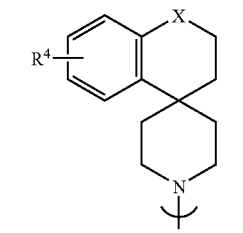
(d)

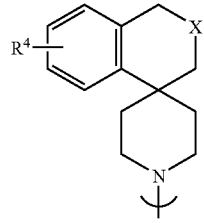
(e)

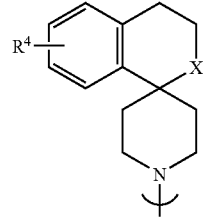
(f)

each X is the same or different and is $CR^{iii}R^{iv}$, $NR^{iii}$ or O, wherein in (a), only one X can be O, the other being $CR^{iii}R^{iv}$ or $NR^{iii}$;

$R^1$ is H,
  $C_{1-6}$-alkyl optionally substituted by CN,
  aryl, 5 or 6 membered heteroaryl or sulfonylaryl each of which is optionally substituted by one or more B,
  —$(CH_2)_m$—$R^a$ wherein $R^a$ is:
    $OR^i$,
    $NR^iR^{ii}$, or
    $C_{3-6}$-cycloalkyl, 4 to 7 membered-heterocycloalkyl, aryl, or 5 or 6 membered heteroaryl eaqch of which is optionally substituted by one or more B,
  or —$(CH_2)_n$—(CO)—$R^b$ or —$(CH_2)_n$-$(SO_2)$—$R^b$, wherein $R^b$ is:
    $C_{1-6}$-alkyl,
    $C_{1-6}$-alkoxy,
    $C_{3-6}$-cycloalkyl,
    —$(CH_2)_m$—$NR^{iii}R^{iv}$,
    $NR^iR^{ii}$, or
    $C_{3-6}$-cycloalkyl, 4 to 7 membered-heterocycloalkyl, aryl, or 5 or 6 membered heteroaryl each of which is optionally substituted by one or more B, or $R^1$ and $R^3$ together with the indole ring to which they are attached form a 5 or 6 membered heterocycloalkyl which is optionally substituted by (CO);

there can be one or more $R^2$ wherein each
$R^2$ is independently H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, benzyloxy, or $C_{1-6}$-haloalkyl, or two $R^2$ together with the indole ring to which they are attached form an oxo or dioxo bridge;

$R^3$ is H,
  halo,
  —(CO)—$R^c$, wherein $R^1$ is:
    $C_{1-6}$-alkyl,
    —$(CH_2)_n$—$NR^iR^{ii}$,
    —$(CH_2)_n$—$NR^{iii}R^{iv}$, or
    5 or 6 membered heterocycloalkyl optionally substituted by $C_{1-6}$-alkyl,
  or $C_{1-6}$-alkyl or aryl, each of which is optionally substituted by halo, —O(CO)—C$_{1-6}$-alkyl, or —NH(CO)R$^d$, wherein R$^d$ is C$_{1-6}$-alkyl optionally substituted by halo or nitro, or R$^d$ is aryl or a 5 or 6 membered heteroaryl, each of which is optionally substituted by halo, nitro, C$_{1-6}$-alkyl or C$_{1-6}$-haloalkyl;

there can be one or more R$^4$ wherein each

R$^4$ is independently H, halo, C$_{1-6}$ alkyl, C$_{1-6}$ alkoxy, or CN, or two R$^4$ together with the phenyl ring to which they are attached form an oxo or dioxo bridge;

B is halo,
  CN,
  NR$^i$R$^{ii}$,
  C$_{1-6}$-alkyl optionally substituted by CN, halo or C$_{1-6}$-alkoxy,
  C$_{1-6}$-alkoxy,
  C$_{1-6}$-haloalkoxy,
  C$_{3-6}$-cycloalkyl,
  —C(O)O—C$_{1-6}$-alkyl,
  —C(O) NR$^i$R$^{ii}$,
  —C(O)—C$_{1-6}$-alkyl,
  —S(O)2—C$_{1-6}$-alkyl,
  —S(O)$_2$—NR R ,
  (CR$^{iii}$R$^{iv}$)n-phenyl, or
  (CR$^{iii}$R$^{iv}$)n-5 or 6 membered heteroaryl, wherein the phenyl or 5 or 6 membered heteroaryl moiety is optionally substituted by one or more substituent(s) selected from the group consisting of:
    halo, CN, NR$^i$R$^{ii}$, C$_{1-6}$-alkyl optionally substituted by CN or C$_{1-6}$-alkoxy, C$_{1-6}$-alkoxy, C$_{1-6}$-haloalkoxy, C$_{3-6}$-cycloalkyl, —C(O)O—C$_{1-6}$-alkyl, —C(O)—NR$^i$R$^{ii}$, —C(O)—C$_{1-6}$-alkyl, —S(O)$_2$—C$_{1-6}$-alkyl, and —S(O)$_2$—NR$^i$R$^{ii}$;

R$^i$ and R$^{ii}$ are each independently H, C$_{1-6}$-alkyl, C$_{1-6}$-alkylene-NR$^{iii}$R$^{iv}$, —(CO)O—C$_{1-6}$-alkyl, —C(O)—NR$^{iii}$R$^{iv}$, —C(O)—C$_{1-6}$-alkyl, —S(O)$_2$—C$_{1-6}$-alkyl or —S(O)$_2$—NR$^{iii}$R$^{iv}$;

R$^{iii}$ is H, C$_{1-6}$-alkyl or C$_{1-6}$-alkylene-N(R$^{iv}$)$_2$;
R$^{iv}$ is H or C$_{1-6}$-alkyl;
m is 1 to 6;
n is 0 to 4;

and pharmaceutically acceptable salts thereof.

In detail, a certain embodiment of the present invention relates to compounds of the general formula (I):

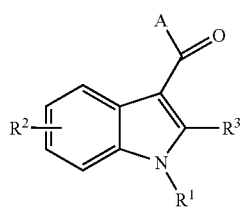

(I)

wherein

A is selected from the following groups (a), (b), (c), (d), (e) and (f):

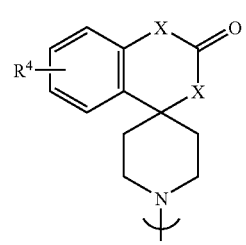

(a)

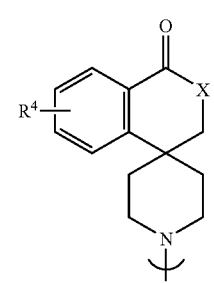

(b)

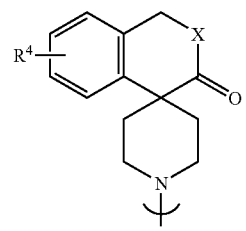

(c)

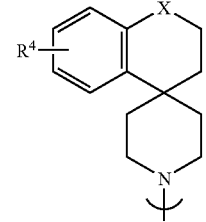

(d)

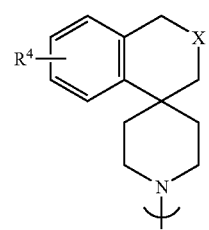

(e)

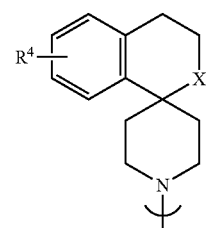

(f)

each X is the same or different and is CR$^{iii}$R$^{iv}$, NR$^{iii}$ or O, wherein in (a), only one X can be O, the other being CR$^{iii}$R$^{iv}$ or NR$^{iii}$;

$R^1$ is H, $C_{1-6}$-alkyl optionally substituted by CN, aryl, 5 or 6 membered heteroaryl or sulfonylaryl each of which is optionally substituted by one or more B, —$(CH_2)_m$—$R^a$ wherein $R^a$ is:

$OR^i$, $NR^iR^{ii}$, or $C_{3-6}$-cycloalkyl, 4 to 7 membered-heterocycloalkyl, aryl, or 5 or 6 membered heteroaryl each of which is optionally substituted by one or more B, or —$(CH_2)_n$—(CO)—$R^b$ or —$(CH_2)_n$-$(SO_2)$—$R^b$, wherein $R^b$ is:

$C_{1-6}$-alkyl, $C_{1-6}$-alkoxy, $C_{3-6}$-cycloalkyl,

—$(CH_2)_m$—$NR^{iii}R^{iv}$, $NR^iR^{ii}$, or $C_{3-6}$-cycloalkyl, 4 to 7 membered-heterocycloalkyl, aryl, or 5 or 6 membered heteroaryl each of which is optionally substituted by one or more B, or $R^1$ and $R^3$ together with the indole ring to which they are attached form a 5 or 6 membered heterocycloalkyl which can be substituted by (CO);

there can be one or more $R^2$ wherein each $R^2$ is independently H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, or benzyloxy, or two $R^2$ together with the indole ring to which they are attached form an oxo or dioxo bridge;

$R^3$ is H, halo,

—(CO)—$R^c$, wherein $R^c$ is:

$C_{1-6}$-alkyl,

—$(CH_2)_n$—$NR^iR^{ii}$,

—$(CH_2)_n$—$NR^{iii}R^{iv}$, or 5 or 6 membered heterocycloalkyl optionally substituted by $C_{1-6}$-alkyl, or $C_{1-6}$-alkyl or aryl, each of which is optionally substituted by halo, —O(CO)—$C_{1-6}$-alkyl, or —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

there can be one or more $R^4$ wherein each $R^4$ is independently H, halo, $C_{1-6}$ alkyl, $C_{1-6}$ alkoxy, or CN, or two $R^4$ together with the phenyl ring to which they are attached form an oxo or dioxo bridge;

B is halo,

CN, $NR^iR^{ii}$, $C_{1-6}$-alkyl optionally substituted by CN, halo or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O) $NR^iR^{ii}$, —C(O)—$C_{1-6}$-alkyl, —$S(O)_2$—$C_{1-6}$-alkyl, —$S(O)_2$—$NR^iR^{ii}$, $(CR^{iii}R^{iv})_n$-phenyl, or $(CR^{iii}R^{iv})_n$-5 or 6 membered heteroaryl, wherein the phenyl or 5 or 6 membered heteroaryl moiety is optionally substituted by one or more substituent(s) selected from the group consisting of:

halo, CN, $NR^iR^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—$NR^iR^{ii}$, —C(O)—$C_{1-6}$-alkyl, —$S(O)_2$—$C_{1-6}$-alkyl, and —$S(O)_2$—$NR^iR^{ii}$;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl or —$S(O)_2$—$NR^{iii}R^{iv}$;

$R^{iii}$ and $R^{iv}$ are each independently H or $C_{1-6}$-alkyl;

m is 1 to 6; and n is 0 to 4;

and pharmaceutically acceptable salt thereof.

In a certain embodiment of the invention, A, X, $R^1$ to $R^4$, $R^a$, $R^b$, $R^c$, $R^d$, B, $R^i$, $R^{ii}$, m and n are as described above, and $R^{iii}$ is H, $C_{1-6}$-alkyl or $C_{1-6}$-alkylene-$N(R^{iv})_2$; and $R^{iv}$ is H or $C_{1-6}$-alkyl.

In certain embodiments of the invention, $R^1$ is selected from the group consisting of

H, $C_{1-6}$-alkyl optionally substituted by CN, aryl or 5 or 6 membered heteroaryl each of which is optionally substituted by one or more B, —$(CH_2)_m$—$R^a$ wherein $R^a$ is:

4 to 7 membered-heterocycloalkyl or aryl, each of which is optionally substituted by one or more B, —$(CH_2)_n$—(CO)—$R^b$, wherein $R^b$ is:

$C_{1-6}$-alkoxy, $NR^iR^{ii}$, or 4 to 7 membered-heterocycloalkyl, aryl, or 5 or 6 membered heteroaryl each of which is optionally substituted by one or more B;

B is halo, $C_{1-6}$-alkyl or phenyl;

$R^i$ and $R^{ii}$ are each independently H or $C_{1-6}$-alkyl.

In certain embodiments of the invention, $R^2$ is one or more residues selected from the group consisting of H, halo, $C_{1-6}$-alkyl, and $C_{1-6}$-alkoxy. Preferably, $R^2$ is located at the 5 and/or 6-position of the indole. More preferably, $R^2$ is —OMe in the 5-position; or F in the 5-position and Cl in the 6-position; or Me in the 5-position and Cl in the 6-position; or H in the 6-position; or Cl in the 6-position of the indole. Even more preferably, $R^2$ is Cl in the 6-position of the indole; or H in the 6-position of the indole. Most preferably, $R^2$ is Cl in the 6-position of the indole.

In certain embodiments of the invention, $R^3$ is hydrogen or $C_{1-6}$-alkyl.

Preferably, $R^4$ is hydrogen.

A further embodiment of the invention includes compounds of formula (I) as described herein, or pharmaceutically acceptable salts thereof, with the proviso that not all $R^1$, $R^2$, and $R^3$ are H at the same time.

A further embodiment of the invention includes compounds of formula (I) as described herein, or pharmaceutically acceptable salts thereof, with the proviso that not all $R^1$, $R^2$, $R^3$ and $R^4$ are H at the same time.

In certain embodiments of the invention, group (a) of the compound of formula (I) is selected from (a') and (a"):

(a')

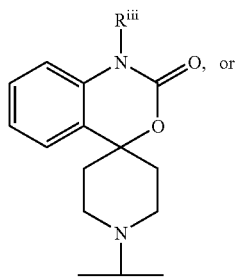

(a")

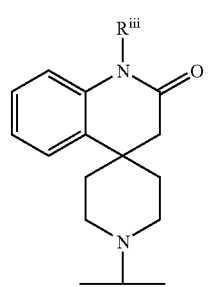

wherein R$^{iii}$ is H, C$_{1-6}$-alkyl or C$_{1-6}$-alkylene-N(R$^{iv}$)2 and R$^{iv}$ is H or C$_{1-6}$-alkyl; preferably, R$^{iii}$ is H or C$_{1-6}$-alkyl; most preferably, R$^{iii}$ is H.

As can be seen from the definition of A in the compounds of formula (I), said compounds of formula (I) encompass the compounds of formulae (I-a), (I-b), (I-c), (I-d), (I-e) and (I-f) as follows:

(I-a)

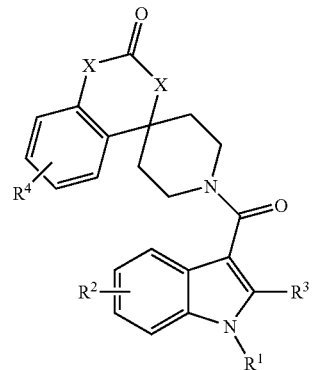

(I-b)

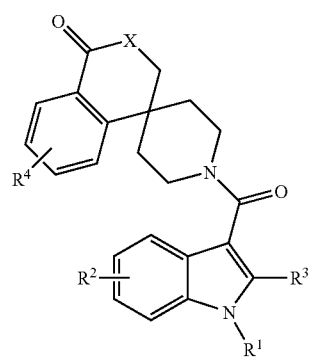

(I-c)

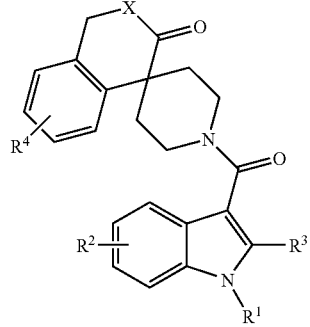

(I-d)

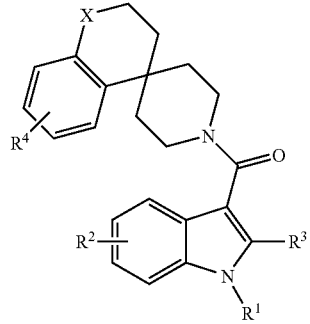

(I-e)

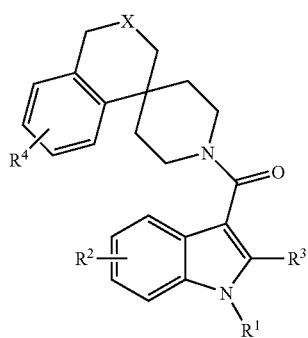

(I-f)

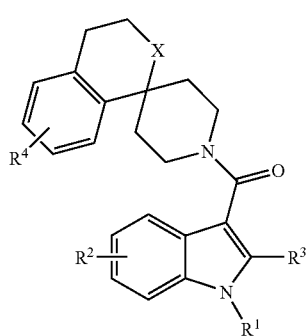

wherein R$^1$ to R$^4$ and X are as defined hereinabove in connection with formula (I).

In a certain embodiment the compounds of the invention are those compounds of formula (I-a):

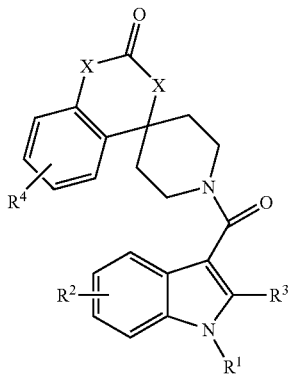

(I-a)

wherein:

each X can be the same or different and is $CR^{iii}R^{iv}$, $NR^{iii}$ or O, wherein only one X can be O, the other being $CR^{iii}R^{iv}$ or $NR^{iii}$;

$R^1$ is H,

C$_{1-6}$-alkyl optionally substituted by CN, aryl optionally substituted by one or more B, —(CH$_2$)$_m$—R$^a$ wherein R$^a$ is:

NR$^i$R$^{ii}$, or aryl optionally substituted by one or more B, or —(CH$_2$)$_n$—(CO)—R$^b$ or —(CH$_2$)$_n$-(SO$_2$)—R$^b$, wherein R$^b$ is:

C$_{1-6}$-alkoxy,

NR$^i$R$^{ii}$, or 4 to 7 membered-heterocycloalkyl, aryl, or 5 or 6 membered heteroaryl each of which is optionally substituted by one or more B, there can be one or more R$^2$ wherein each R$^2$ is independently H or halo, e.g. Cl, R$^3$ is H or C$_{1-6}$-alkyl, there can be one or more R$^4$ wherein each R$^4$ is independently H, halo, C$_{1-6}$ alkyl, C$_{1-6}$ alkoxy, or CN;

B is halo,

CN,

NR$^i$R$^{ii}$,

C$_{1-6}$-alkyl optionally substituted by CN, halo or C$_{1-6}$-alkoxy,

C$_{1-6}$-alkoxy,

C$_{1-6}$-haloalkoxy,

C$_{3-6}$-cycloalkyl,

—C(O)O—C$_{1-6}$-alkyl,

—C(O) NR$^i$R$^{ii}$,

—C(O)—C$_{1-6}$-alkyl,

—S(O)$_2$—C$_{1-6}$-alkyl,

—S(O)$_2$—NR$^i$R$^{ii}$, (CR$^{iii}$R$^{iv}$)n-phenyl or (CR$^{iii}$R$^{iv}$)$_n$-5 or 6 membered heteroaryl, wherein the phenyl or 5 or 6 membered heteroaryl moiety is optionally substituted by one or more substituent(s) selected from the group consisting of: halo, CN, NR$^i$R$^{ii}$, C$_{1-6}$-alkyl optionally substituted by CN or C$_{1-6}$-alkoxy, C$_{1-6}$-alkoxy, C$_{1-6}$-haloalkoxy, C$_{3-6}$-cycloalkyl, —C(O)O—C$_{1-6}$-alkyl, —C(O)—NR$^i$R$^{ii}$, —C(O)—C$_{1-6}$-alkyl, —S(O)$_2$—C$_{1-6}$-alkyl, and —S(O)$_2$—NR$^i$R$^{ii}$;

R$^i$ and R$^{ii}$ are each independently H, C$_{1-6}$-alkyl, C$_{1-6}$-alkylene-NR$^{iii}$R$^{iv}$, —(CO)O—C$_{1-6}$-alkyl, —C(O)—NR$^{iii}$R$^{iv}$, —C(O)—C$_{1-6}$-alkyl, —S(O)$_2$—C$_{1-6}$-alkyl or —S(O)$_2$—NR$^{iii}$R$^{iv}$;

R$^{iii}$ is H, C$_{1-6}$-alkyl or C$_{1-6}$-alkylene-N(R$^{iv}$)$_2$;

R$^{iv}$ is H or C$_{1-6}$-alkyl;

m is 1 to 6; and n is 0 to 4;

and pharmaceutically acceptable salts thereof.

In this embodiment, preferably (a) is selected from (a') and (a").

In a certain embodiment the compounds of formula (I-a) are those compounds wherein R$^1$ is H, for example the following compounds:

1'-[(6-Chloro-1H-indol-3-yl)carbonyl]spiro[3,1-benzoxazine-4,4'-piperidin]-2(1H)-one;

6'-Bromo-1-(1H-indol-3-ylcarbonyl)-1'H-spiro[piperidine-4,4'-quinolin]-2'(3'H)-one;

6-Chloro-1'-[(6-chloro-1H-indol-3-yl)carbonyl]-1-[2-(dimethylamino)ethyl]spiro[3,1-benzoxazine-4,4'-piperidin]-2(1H)-one; and 6-Chloro-1'-[(6-chloro-1H-indol-3-yl)carbonyl]spiro[3,1-benzoxazine-4,4'-piperidin]-2(1H)-one.

In a certain embodiment the compounds of formula (I-a) are those compounds wherein R$^1$ is aryl optionally substituted by one or more B and B is as defined hereinabove for formula (I-a), for example the following compound: 1'-{[6-chloro-1-(3,5-difluorophenyl)-1H-indol-3-yl]carbonyl}spiro[3,1-benzoxazine-4,4'-piperidin]-2(1H)-one.

In a certain embodiment the compounds of formula (I-a) are those compounds wherein R$^1$ is —(CH$_2$)$_m$—R$^a$ wherein R$^a$ is CN, NR$^i$R$^{ii}$, or aryl optionally substituted by one or more B and m, R$^i$, R$^{ii}$ and B are as defined for formula (I-a) hereinabove, for example the following compounds:

1'-{[6-Chloro-1-(3,5-difluorobenzyl) -1H-indol-3-yl]carbonyl}spiro[3,1-benzoxazine-4,4'-piperidin]-2(1H)-one;

1'-{[6-Chloro-1-(3-fluorobenzyl)-1H-indol-3-yl]carbonyl}spiro[3,1-benzoxazine-4,4'-piperidin]-2(1H)-one;

3-{6-Chloro-3-[(2-oxo-1,2-dihydro-1'H-spiro[3,1-benzoxazine-4,4'-piperidin]-1'-yl)carbonyl]-1H-indol-1-yl}propanenitrile; and 2-{6-Chloro-3-[(2-oxo-1,2-dihydro-1'H-spiro[3,1-benzoxazine-4,4'-piperidin]-1'-yl)carbonyl]-1H-indol-1-yl}propanenitrile.

In a certain embodiment the compounds of formula (I-a) are those compounds wherein R$^1$ is —(CH$_2$)$_n$—(CO)—R$^b$ or —(CH$_2$)$_n$-(SO$_2$)—R$^b$, wherein R$^b$ is C$_{1-6}$-alkoxy, NR$^i$R$^{ii}$, 4 to 7 membered-heterocycloalkyl, aryl, or 5 or 6 membered heteroaryl which are optionally substituted by one or more B and n, R$^i$, R$^{ii}$ and B are as defined for formula (I-a) hereinabove, for example the following compounds:

1'-{[6-Chloro-1-(3-fluorobenzoyl)-1H-indol-3-yl]carbonyl}spiro[3,1-benzoxazine-4,4'-piperidin]-2(1H)-one;

1'-{[6-Chloro-1-(2-fluorobenzoyl)-1H-indol-3-yl]carbonyl}spiro[3,1-benzoxazine-4,4'-piperidin]-2(1H)-one;

1'-{[6-Chloro-1-(2,3-difluorobenzoyl)-1H-indol-3-yl]carbonyl}spiro[3,1-benzoxazine-4,4'-piperidin]-2(1H)-one;

1'-({6-Chloro-1-[(3,5-difluorophenyl)sulfonyl]-1H-indol-3-yl}carbonyl)spiro[3,1-benzoxazine-4,4'-piperidin]-2(1H)-one;

1'-({6-Chloro-1-[2-(3-fluorophenyl)-2-oxoethyl]-1H-indol-3-yl}carbonyl)spiro[3,1-benzoxazine-4,4'-piperidin]-2(1H)-one;

1'-({6-Chloro-1-[2-(3,4-difluorophenyl)-2-oxoethyl]-1H-indol-3-yl}carbonyl)spiro[3,1-benzoxazine-4,4'-piperidin]-2(1H)-one;

1'-{[1-(Biphenyl-3-ylcarbonyl)-6-chloro-1H-indol-3-yl]carbonyl}spiro[3,1-benzoxazine-4,4'-piperidin]-2(1H)-one;

1'-{[6-Chloro-1-(2-oxo-2-piperidin-1-ylethyl)-1H-indol-3-yl]carbonyl}spiro[3,1-benzoxazine-4,4'-piperidin]-2(1H)-one;

1'-{[6-Chloro-1-(2-morpholin-4-yl-2-oxoethyl)-1H-indol-3-yl]carbonyl}spiro[3,1-benzoxazine-4,4'-piperidin]-2(1H)-one;

2-{6-Chloro-3-[(2-oxo-1,2-dihydro-1'H-spiro[3,1-benzoxazine-4,4'-piperidin]-1'-yl)carbonyl]-1H-indol-1-yl}-N,N-dimethylacetamide;

2-{6-Chloro-3-[(2-oxo-1,2-dihydro-1'H-spiro[3,1-benzoxazine-4,4'-piperidin]-1'-yl)carbonyl]-1H-indol-1-yl}-N,N-diethylacetamide;

1'-{[6-Chloro-1-(piperidin-1-ylcarbonyl)-1H-indol-3-yl]carbonyl}spiro[3,1-benzoxazine-4,4'-piperidin]-2(1H)-one;

tert-Butyl {6-chloro-3-[(2-oxo-1,2-dihydro-1'H-spiro[3,1-benzoxazine-4,4'-piperidin]-1'-yl)carbonyl]-1H-indol-1-yl}acetate;

1'-{[6-Chloro-1-(3,5-difluorobenzoyl)-1H-indol-3-yl]carbonyl}spiro[3,1-benzoxazine-4,4'-piperidin]-2(1H)-one;

1'-({6-Chloro-1-[2-(3,5-difluorophenyl)-2-oxoethyl]-1H-indol-3-yl}carbonyl)spiro[3,1-benzoxazine-4,4'-piperidin]-2(1H)-one;

1'-({6-Chloro-1-[2-(2-fluorophenyl)-2-oxoethyl]-1H-indol-3-yl}carbonyl)spiro[3,1-benzoxazine-4,4'-piperidin]-2(1H)-one;

1'-{[6-Chloro-1-(2-oxo-2-pyridin-2-ylethyl)-1H-indol-3-yl]carbonyl}spiro[3,1-benzoxazine-4,4'-piperidin]-2(1H)-one; and 1'-({6-Chloro-1-[2-(5-methyl-2-phenyl-1,3-oxazol-4-yl)-2-oxoethyl]-1H-indol-3-yl}carbonyl)spiro[3,1-benzoxazine-4,4'-piperidin]-2(1H)-one.

In the compounds of formula (I-a), and independently of the definitions of $R^1$ to $R^4$, one X can be NH and the other one O.

In a certain embodiment of the invention, formula (I) encompasses the compound of formula (I-b) wherein X and $R^1$ to $R^4$ are as defined above, preferably
X is NH;
$R^1$ is H,
  $C_{1-6}$-alkyl optionally substituted by CN,
  aryl or 5 or 6 membered heteroaryl each of which is optionally substituted by one or more B,
  —$(CH_2)_m$—$R^a$ wherein $R^a$ is:
    4 to 7 membered-heterocycloalkyl or aryl, each of which is optionally substituted by one or more B,
  or —$(CH_2)_n$—(CO)—$R^b$, wherein $R^b$ is:
    $C_{1-6}$-alkoxy,
    $NR^iR^{ii}$, or
    4 to 7 membered-heterocycloalkyl, aryl, or 5 or 6 membered heteroaryl each of which is optionally substituted by one or more B;
B is halo, $C_{1-6}$-alkyl or phenyl;
$R^i$ and $R^{ii}$ are independently H or $C_{1-6}$-alkyl;
more preferably, $R^1$ is —$(CH_2)_n$—(CO)—$R^b$, wherein R is $NR^iR^{ii}$ and $R^i$ and $R^{ii}$ are independently H or $C_{1-6}$-alkyl;
$R^2$ is H or halo;
$R^3$ is H; and
$R^4$ is H.

An example of a compound of formula (I-B) is 2-{6-chloro-3-[(1-oxo-2,3-dihydro-1H,1'H-spiro[isoquinoline-4,4'-piperidin]-1'-yl)carbonyl]-1H-indol-1-yl}-N-methylacetamide.

The invention also encompasses pharmaceutical compositions which comprise a compound of formula (I), (I-a), (I-b), (I-c), (I-d), (I-e) or (I-f) or a pharmaceutically acceptable salt thereof and a pharmaceutically acceptable carrier.

The invention also encompasses methods for the treatment of dysmenorrhea, hypertension, chronic heart failure, inappropriate secretion of vasopressin, liver cirrhosis, nephrotic syndrome, obsessive compulsive disorder, anxiety and depressive disorders which comprise administering to an individual a therapeutically effective amount of a compound of formula (I), (I-a), (I-b), (I-c), (I-d), (I-e) or (I-f) or a pharmaceutically acceptable salt thereof.

In a certain embodiment, the compounds of formula (I) of the invention wherein $R^1$ is H can be manufactured according to a process comprising the step of reacting a compound of formula (II-a):

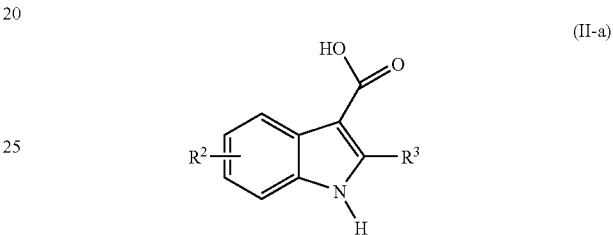

with a compound of formula A-H to obtain the compound of formula (I), wherein $R^1$ is H and A, $R^2$ and $R^3$ are as defined hereinabove.

In another embodiment, the compounds of formula (I) of the invention can be manufactured according to a process comprising the step of reacting a compound of formula (I-1):

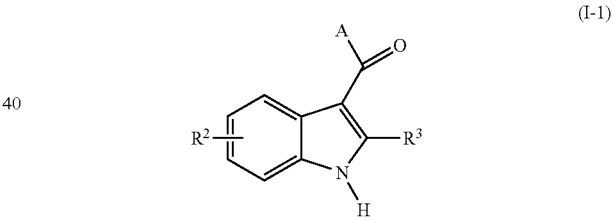

with an electrophile compound of formula $R^1$-Z to obtain the compound of formula (I), wherein A, $R^1$, $R^2$ and $R^3$ are as defined hereinabove and Z is halo, preferably Br or Cl.

In still another embodiment, the compounds of formula (I) of the invention can be manufactured according to a process comprising the step of reacting a compound of formula (II-b):

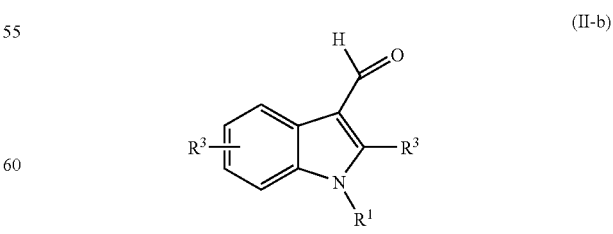

with a compound of formula A-H to obtain the compound of formula (I), wherein $R^1$, $R^2$, $R^3$, and A are as defined hereinabove.

The preparation of the compounds of the invention of formulae (I), (I-a), (I-b), (I-c), (I-d), (I-e) and (I-f) is described more in details with the following general schemes A, B and C, wherein R¹, R², R³ and A are as defined hereinabove:

Alternatively, (II-a) can be prepared following the sequence in scheme C. The spiropiperidine derivatives A-H are either commercially available, either prepared using published procedures or prepared using procedures described hereinafter in the examples.

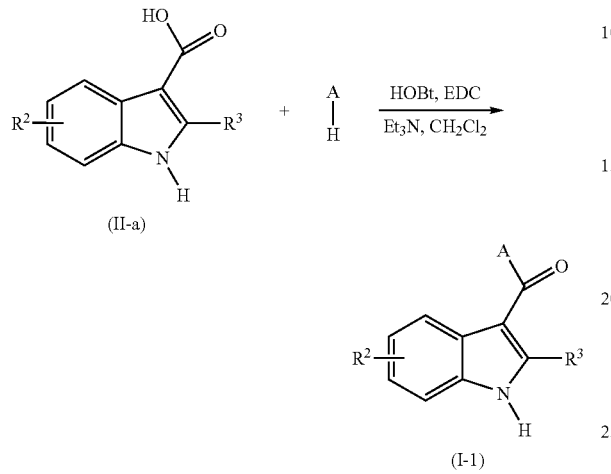

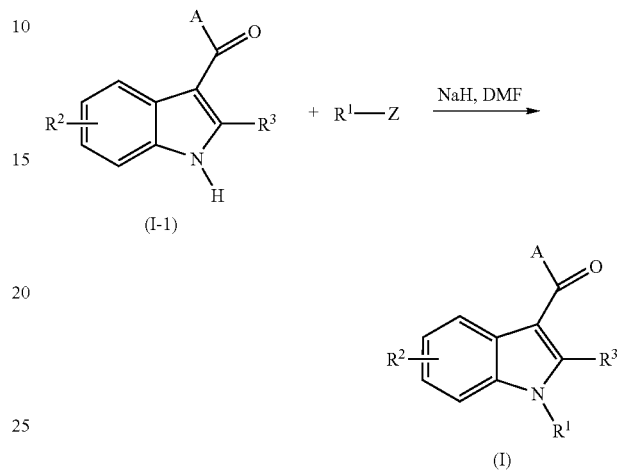

General Procedure A

Compounds of formula (I-1) (compounds of formula (I) wherein R¹ is H) can be prepared via an amide coupling between an indole 3-carboxylic acid (II-a) and a spiropiperidine (A-H), see e.g. the general procedure for the amide coupling hereinafter. Indole 3-carboxylic acids (II-a) are either commercially available or readily prepared using a procedure described in. *J. Med. Chem.* 1991, 34, 140.

General Procedure B

Compounds of formula (I) wherein R¹ is different from H, can be prepared by an alkylation of an indole derivative (I-1) with an electrophile R¹-Z, wherein Z is halo, (commercially available) using standard procedures. Derivatives (I-1) are prepared are prepared using the method described in the general scheme A.

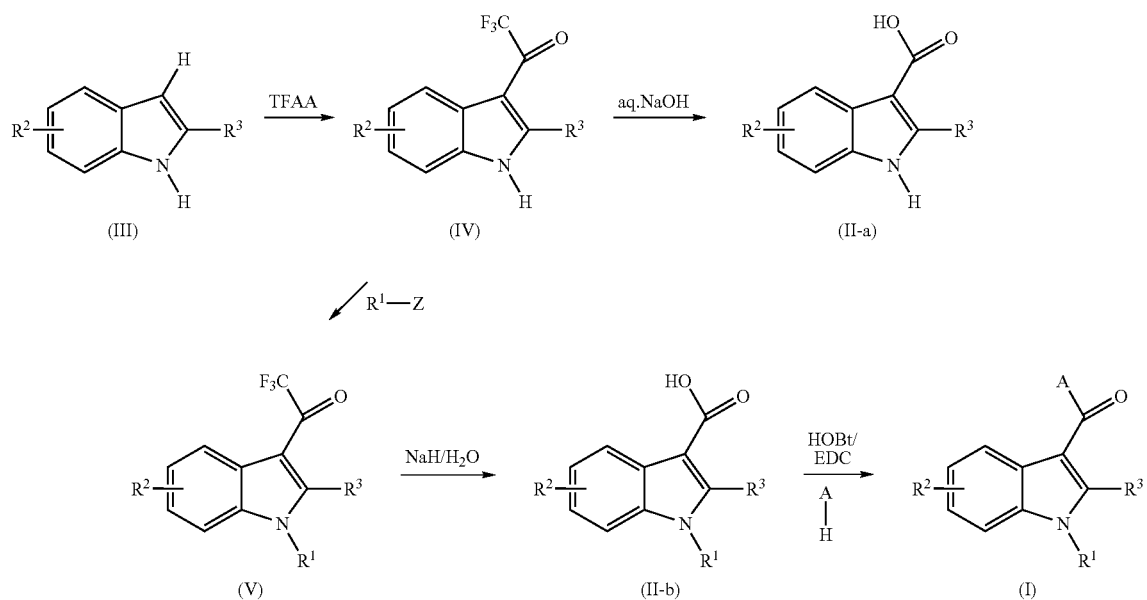

General Procedure C

The treatment of an indole (III) with trifluoroacetic anhydride gives (IV), which can be hydrolyzed to the corresponding 3-carboxylic acid indole (II-a). Alternatively, (IV) can be further elaborated into (V) by coupling with a reagent $R^1$-Z, wherein Z is halo, using well known procedure. The hydrolysis of (V) affords (II-b), which under standard amide coupling with A-H afford derivatives (I).

The general schemes and corresponding procedures presented hereinabove are further illustrated with the preparation of the compounds of the invention hereinafter.

Results—V1a Activity

Material & Method

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lysis buffer (50 mM HEPES, 1 mM EDTA, 10 mM MgCl2 adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43'000 g at 4° C. (19'000 rpm). The pellet is resuspended in 12.5 ml Lysis buffer+12.5 ml Sucrose 20% and homogenized using a Polytron for 1-2 min. The protein concentration is determined by the Bradford method and aliquots are stored at −80° C. until use. For binding studies 60 mg Yttrium silicate SPA beads (Amersham) are mixed with an aliquot of membrane in binding buffer (50 mM Tris, 120 mM NaCl, 5 mM KCl, 2 mM CaCl2, 10 mM MgCl2) for 15 minutes with mixing. 50 ul of bead/membrane mixture is then added to each well of a 96 well plate, followed by 50 ul of 4 nM 3H-Vasopressin (American Radiolabeled Chemicals). For total binding measurement 100 ul of binding buffer are added to the respective wells, for non-specific binding 100 ul of 8.4 mM cold vasopressin and for compound testing 100 ul of a serial dilution of each compound in 2% DMSO. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an IC 50 the curve is fitted using a non-linear regression model (XLfit) and the Ki is calculated using the Cheng-Prussoff equation.

| Example | Ki (nM) [human V1a] |
|---|---|
| 1 | 32 |
| 2 | 2053 |
| 3 | 402 |
| 4 | 310 |
| 5 | 130 |
| 6 | 118 |
| 7 | 117 |
| 8 | 136 |

| Example | Ki (nM) [human V1a] |
|---|---|
| 10 | 3 |
| 11 | 5 |
| 12 | 7 |
| 13 | 8 |
| 15 | 7 |
| 16 | 20 |
| 17 | 5.7 |
| 18 | 6 |
| 19 | 46 |
| 20 | 10 |
| 21 | 88 |
| 22 | 200 |
| 23 | 2 |
| 24 | 10 |
| 25 | 28 |
| 26 | 8 |
| 27 | 29 |
| 28 | 166 |

The present invention also provides pharmaceutical compositions containing compounds of the invention, for example compounds of formula (I) and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. gelatinLactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc/ Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

Compounds of formula (I) have a good activity on the V1a receptor. Therefore, the invention provides methods for treating dysmenorrhea, hypertension, chronic heart failure, inappropriate secretion of vasopressin, liver cirrhosis, nephrotic syndrome, obsessive compulsive disorder, anxiety and depressive disorders which comprise administering to an individual a therapeutically effective amount of a compound of formula (I) or a pharmaceutically acceptable salt thereof.

In particular, the invention provides a method for treating anxiety which comprises administering to an individual a therapeutically effective amount of a compound of formula (I) or a pharmaceutically acceptable salt thereof. The invention provides a method for treating depressive disorders which comprises administering to an individual a therapeutically effective amount of a compound of formula (I) or a pharmaceutically acceptable salt thereof.

The dosage at which compounds of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

The following Examples illustrate the present invention without limiting it. All temperatures are given in degrees Celsius.

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C.

Thereupon, the finely powdered active substance is added thereto and stirred until it has dispersed completely. The mixture is poured into suppository moulds of suitable size, left to cool; the suppositories are then removed from the moulds and packed individually in wax paper or metal foil.

EXAMPLES

Examples of Compounds of Formula (I-1)

General Procedure for the Amide Coupling

To a stirred solution of an indole-3-carboxylic acid derivative (1 mmol) in 10 ml $CH_2Cl_2$ was added (1.3 mmol) EDC, (1.3 mmol) HOBt, (1.3 mmol) $Et_3N$ and (1 mmol) of the amine derivative. The mixture was stirred overnight at RT and then poured onto water and extracted with $CH_2Cl_2$. The combined organic phases were dried over $Na_2SO_4$ and concentrated in vacuo. Flash chromatography or preparative HPLC afforded the title compound.

Where references are cited in the examples, the example was performed using the starting material listed with the reactants and conditions cited in the reference. All procedures in such references are well known to those of ordinary skill in the art. All journal references cited herein are incorporated by reference.

Example 1

1'-[(6-Chloro-1H-indol-3-yl)carbonyl]spiro[3,1-benzoxazine-4,4'-piperidin]-2(1H)-one

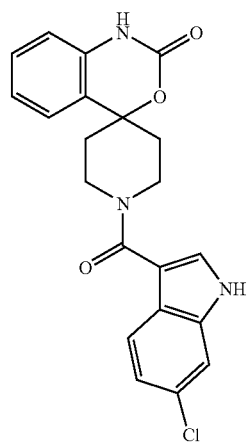

Amide coupling:—Amine: spiro[3,1-benzoxazine-4,4'-piperidin]-2(1H)-one (*J. Med. Chem.*, 1983, 26(5), 657)

Acid: 6-Chloro-1H-indole-3-carboxylic acid

ES-MS m/e (%): 396.1 (M+H$^+$).

6-Chloro-1H-indole-3-carboxylic acid

Using a procedure described in *J. Med. Chem.* 1991, 34, 140, from 7.0 g (0.046 mmol) of 6-Chloro-1H-indole was prepared 5.80 g (64%) of 6-chloro-1H-indole-3-carboxylic acid as a light brown solid. ES-MS m/e (%): 194 (M–H$^+$).

Example 2

6'-Bromo-1-(1H-indol-3-ylcarbonyl)-1'H-spiro[piperidine-4,4'-quinolin]-2'(3'H)-one

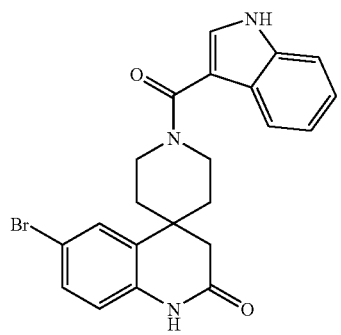

Amide coupling:—Amine: 6'-bromo-1'H-spiro[piperidine-4,4'-quinolin]-2'(3'H)-one

Acid: 1H-Indole-3-carboxylic acid (commercial)

ES-MS m/e (%): 439.1 (M+H$^+$).

6'-Bromo-1'H-spiro[piperidine-4,4'-quinolin]-2'(3'H)-one

A stirred solution of 1'H-spiro[piperidine-4,4'-quinolin]-2'(3'H)-one (described in U.S. Pat. No. 6,013,652) was treated with 7 g of solid sodium bicarbonate, di-tert-butyl pyrocarbonate (7.2g) in 250 mL of methylene chloride and stirred for 2 hours at ambient temperature. The organic layer was separated out and the aqueous part was washed with methylene chloride (2×50 mL). The combined organic extract and washings were washed with brine, dried (anhydrous Na$_2$SO$_4$), concentrated under vacuo to provide a foamy material which was chromatographed over silica (1:3 ethyl acetate-hexane followed by 1:1 ethyl acetate hexane) to provide 1'-(tert-butyloxycarbonyl)spiro(tetrahydroquinol-2-one)-4'-piperidine as a creamish white solid, mp 198° C.; GC-MS (EI) m/z 316.

This compound (10 g, 31.6 mmol) in solution in dry acetonitrile (250 mL) was cooled to −10° C., and N-bromosuccinimide (5.62 g, 31.6 mmol) was added portion wise with stirring. The reaction mixture was stirred for 1 h at −10° C., 2 h at 0° C. and finally at ambient temperature for 24 h. The solvent was removed and the residue dissolved in methylene chloride (500 mL), organic extract washed with brine-water (1:1) (3×50 mL), dried (anhydrous Na$_2$SO$_4$), concentrated in vacuo to provide a creamish white solid which was chromatographed over silica (1:3 ethyl acetate-hexane followed by 1:1 ethyl-acetate hexane) to give 6-bromo-1'-(tert-butyloxycarbonyl) spiro (tetrahydroquinol-2-one)-4'-piperidine (11.8 g, 94%) as a white solid of mp 226° C.; GC-MS (EI) m/z (M−100) 294.

This compound (10 g, 25.3 mmol) in 750 mL of methanol, dry HCl was passed for 10 hrs and the stirring was continued for overnight. The reaction mixture was neutralized with liquor ammonia (75 mL) under ice-cold condition. Methanol and excess ammonia were removed under vacuo and the residue dissolved in methylene chloride (500 mL) followed by the addition of 25 mL of liquor ammonia to dissolve the remaining solid. The organic layer was separated out and the aqueous part washed extracted with methylene chloride (3×150 mL), dried (anhydrous Na$_2$SO$_4$), concentrated under vacuo to provide the title compound as a creamish white solid (7.0 g, 94%) of mp 218° C.; GC-MS (EI) m/z 294.

Example 3

6-Chloro-1'-[(6-chloro-1H-indol-3-yl)carbonyl]-1-[2-(dimethylamino)ethyl]spiro[3,1-benzoxazine-4,4'-piperidin]-2(1H)-one

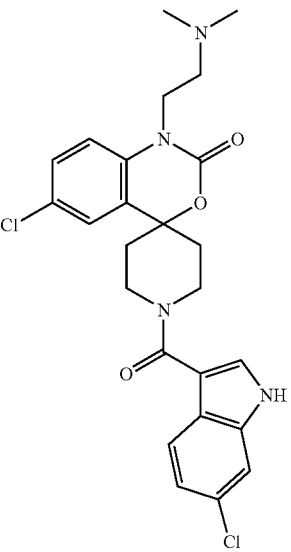

Amide coupling:—Amine: 6-Chloro-1-[2-(dimethylamino)ethyl]spiro[3,1-benzoxazine-4,4'-piperidin]-2(1H)-one (described herein after)

Acid: 6-Chloro-1H-indole-3-carboxylic acid (described in example 2)

ES-MS m/e (%): 501.2 (M+H$^+$).

6-Chloro-1-[2-(dimethylamino)ethyl]spiro[3, 1-benzoxazine-4,4'-piperidin]-2(1H)-one To a solution of 0.100 g (0.283 mmol) tert-butyl 6-chloro-2-oxo-1,2-dihydro-1'H-spiro[3,1-benzoxazine-4,4'-piperidine]-1'-carboxylate (described in WO0122919 A2, and prepared also using the procedure described in "J. Med. Chem.,1983, 26(5), 657" starting from 4-chloro aniline) in 7 ml THF was added 0.025 g (0.566 mmol) NaH. After 30 minutes at RT, 0.063 g (0.566 mmol) (2-chloro-ethyl)-dimethyl-amine was added. The reaction mixture was stirred at 60° C. overnight, then poured onto an aqueous solution of NH$_4$Cl and extracted twice with EtOAc. The combined organic phases were dried over Na$_2$SO$_4$ and concentrated in vacuo yielded 60 mg of a white solid. This crude material was then dissolved in 5 ml CH$_2$Cl$_2$ and 1 ml of TFA was added. After 2 hours at RT, the solvent were removed under vacuo and the resulting oil was taken up in CH$_2$Cl$_2$ and washed with an aqueous solution of NaHCO$_3$. The organic phase was dried with Na$_2$SO$_4$ and concentrated under vacuo to afford 6-chloro-1-[2-(dimethylamino)ethyl]spiro[3,1-benzoxazine-4,4'-piperidin]-2(1H)-one as a white solid.

Example 4

6-Chloro-1'-[(6-chloro-1H-indol-3-yl)carbonyl]spiro[3,1-benzoxazine-4,4'-piperidin]-2(1H)-one

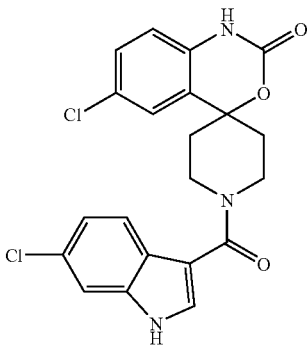

Amide coupling:—Amine: 6-chlorospiro[3,1-benzoxazine-4,4'-piperidin]-2(1H)-one (described in WO0122919 A2, or prepared using the same procedure described in *J. Med. Chem.*, 1983, 26(5), 657 starting with 4-chloro-aniline)

Acid: 6-Chloro-1H-indole-3-carboxylic acid (described in example 2)

ES-MS m/e (%): 431.4 (M+H$^+$).

Example 5

1'-{[6-Chloro-1-(3,5-difluorophenyl)-1H-indol-3-yl]carbonyl}spiro[3,1-benzoxazine-4,4'-piperidin]-2(1H)-one

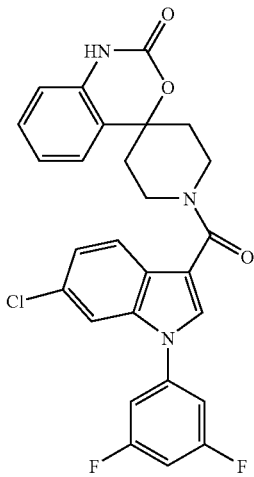

Amide coupling:—Amine: spiro[3,1-benzoxazine-4,4'-piperidin]-2(1H)-one (*J. Med. Chem.*, 1983, 26(5), 657)

Acid: 6-Chloro-1-(3,5-difluoro-phenyl)-1H-indole-3-carboxylic acid

ES-MS m/e (%): 508.0 (M+H$^+$).

6-Chloro-1-(3,5-difluoro-phenyl)-1H-indole-3-carboxylic acid

To a solution of 200 mg (0.807 mmol) 1-(6-chloro-1H-indol-3-yl)-2,2,2-trifluoro-ethanone (prepared from 6-chloro indole and trifluoroacetic anhydride, described in U.S. 2004067939 A1) in 8 ml CH$_2$Cl$_2$, 293 mg (1.615 mmol) Cu(OAc)$_2$, 0.26 ml (3.23 mmol) pyridine and 383 mg (2.42 mmol) 3,5-difluorophenyl boronic acid were added. The reaction mixture was stirred at RT overnight, filtered on decalit, and concentrated under vacuo. Column chromatography over silica (hexane followed by 1:9 ethyl acetate hexane) provided 206 mg (71%) of 1-[6-chloro-1-(3,5-difluoro-phenyl)-1H-indol-3-yl]-2,2,2-trifluoro-ethanone as a light brown solid. This compound was put in suspension in 10 ml H2O and 1.2 g NaOH was added. The reaction mixture was stirred at 70° C. for 2 days, cooled down to RT, and acidified with aqueous HCl (1N) until ph=1. The product was extracted with CH$_2$Cl$_2$, and the organic phase dried over Na$_2$SO4. Evaporation of the solvent under vacuo afforded 120 mg (70%) of 6-chloro-1-(3,5-difluoro-phenyl)-1H-indole-3-carboxylic acid as a white solid.

Example 6

1'-{[6-Chloro-1-(3-fluorobenzoyl)-1H-indol-3-yl]carbonyl}spiro[3,1-benzoxazine-4,4'-piperidin]-2(1H)-one

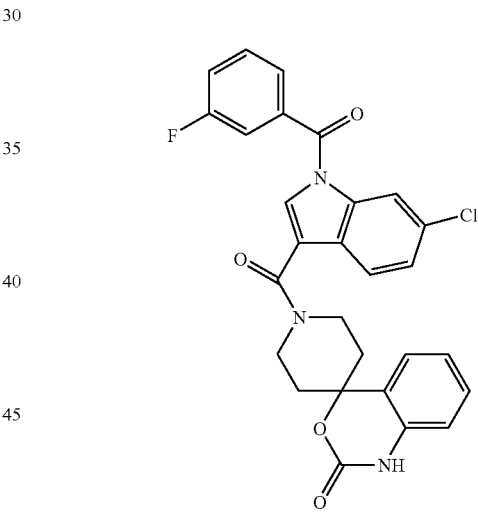

To a solution of 100 mg (0.252 mmol) 1'-[(6-chloro-1H-indol-3-yl)carbonyl]spiro[3,1-benzoxazine-4,4'-piperidin]-2(1H)-one (described in example 1) in dry DMF (5 ml) was added 10 mg NaH (0.25 mmol, 60% in oil). After 15 minutes at RT, 43.9 mg (0.277 mmol) of 3-fluoro-benzoyl chloride was added and stirring continued overnight. The reaction mixture was poured onto an aqueous solution of ammonium chloride, and the product extracted twice with ethyl acetate. The combined organic phases were dried on Na$_2$SO$_4$ and the solvent evaporated under reduced pressure. Purification by preparative HPLC yielded 1'-{[6-chloro-1-(3-fluorobenzoyl)-1H-indol-3-yl]carbonyl}spiro[3,1-benzoxazine-4,4'-piperidin]-2(1H)-one.

ES-MS m/e (%): 518.4 (M+H$^+$).

Example 7

1'-{[6-Chloro-1-(2-fluorobenzoyl)-1H-indol-3-yl]carbonyl}spiro[3,1-benzoxazine-4,4'-piperidin]-2(1H)-one

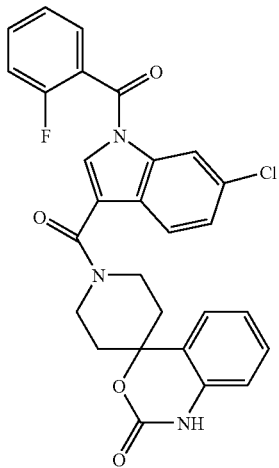

Using the same procedure described in example 6, from 1'-[(6-chloro-1H-indol-3-yl) carbonyl]spiro[3,1-benzoxazine-4,4'-piperidin]-2(1H)-one (described in example 1) and 2-fluoro-benzoyl chloride was prepared 1'-{[6-chloro-1-(2-fluorobenzoyl)-1H-indol-3-yl]carbonyl}spiro[3,1-benzoxazine-4,4'-piperidin]-2(1H)-one.

ES-MS m/e (%): 518.4 (M+H$^+$).

Example 8

1'-{[6-Chloro-1-(2,3-difluorobenzoyl)-1H-indol-3-yl]carbonyl}spiro[3,1-benzoxazine-4,4'-piperidin]-2(1H)-one

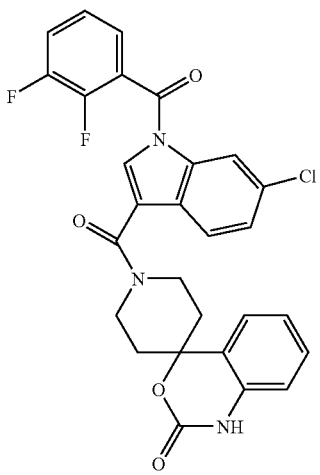

Using the same procedure described in example 6, from 1'-[(6-chloro-1H-indol-3-yl) carbonyl]spiro[3,1-benzoxazine-4,4'-piperidin]-2(1H)-one (described in example 1) and 2,3-difluoro-benzoyl chloride was prepared 1'-{[6-chloro-1-(2,3-difluorobenzoyl)-1H-indol-3-yl]carbonyl}spiro[3,1-benzoxazine-4,4'-piperidin]-2(1H)-one.

ES-MS m/e (%): 536.4 (M+H$^+$).

Example 9

1'-({6-Chloro-1-[(3,5-difluorophenyl)sulfonyl]-1H-indol-3-yl}carbonyl)spiro[3,1-benzoxazine-4,4'-piperidin]-2(1H)-one

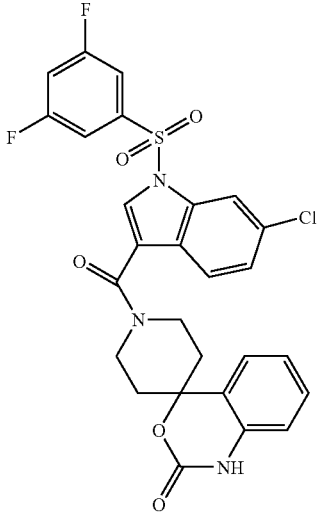

Using the same procedure described in example 6, from 1'-[(6-chloro-1H-indol-3-yl) carbonyl]spiro[3,1-benzoxazine-4,4'-piperidin]-2(1H)-one (described in example 1) and 3,5-difluoro-benzenesulfonyl chloride was prepared 1'-({6-chloro-1-[(3,5-difluorophenyl)sulfonyl]-1H-indol-3-yl}carbonyl)spiro[3,1-benzoxazine-4,4'-piperidin]-2(1H)-one.

ES-MS m/e (%): 572.3 (M+H$^+$).

Example 10

1'-{[6-Chloro-1-(3,5-difluorobenzyl)-1H-indol-3-yl]carbonyl}spiro[3,1-benzoxazine-4,4'-piperidin]-2(1H)-one

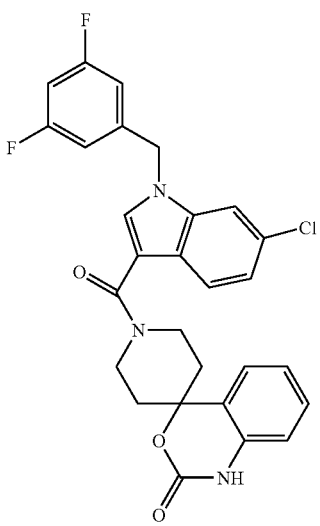

Using the same procedure described in example 6, from 1'-[(6-chloro-1H-indol-3-yl) carbonyl]spiro[3,1-benzoxazine-4,4'-piperidin]-2(1H)-one (described in example 1)

and 1-bromomethyl-3,5-difluoro-benzene was prepared 1'-{[6-chloro-1-(3,5-difluorobenzyl)-1H-indol-3-yl]carbonyl}spiro[3,1-benzoxazine-4,4'-piperidin]-2(1H)-one.

ES-MS m/e (%): 522.4 (M+H⁺).

Example 11

1'-{[6-Chloro-1-(3-fluorobenzyl)-1H-indol-3-yl]carbonyl}spiro[3,1-benzoxazine-4,4'-piperidin]-2(1H)-one

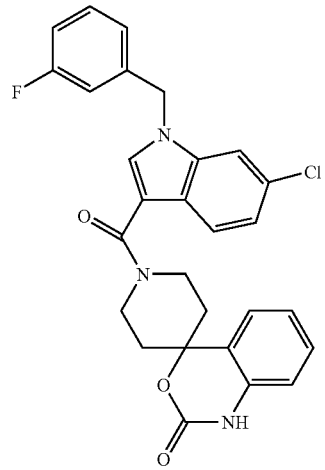

Using the same procedure described in example 6, from 1'-[(6-chloro-1H-indol-3-yl) carbonyl]spiro[3,1-benzoxazine-4,4'-piperidin]-2(1H)-one (described in example 1) and 1-bromomethyl-3-fluoro-benzene was prepared 1'-{[6-chloro-1-(3-fluorobenzyl)-1H-indol-3-yl]carbonyl}spiro[3,1-benzoxazine-4,4'-piperidin]-2(1H)-one.

ES-MS m/e (%): 504.4 (M+H⁺).

Example 12

1'-({6-Chloro-1-[2-(3-fluorophenyl)-2-oxoethyl]-1H-indol-3-yl}carbonyl)spiro[3,1-benzoxazine-4,4'-piperidin]-2(1H)-one

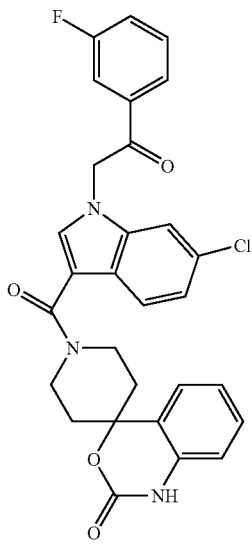

Using the same procedure described in example 6, from 1'-[(6-chloro-1H-indol-3-yl) carbonyl]spiro[3,1-benzoxazine-4,4'-piperidin]-2(1H)-one (described in example 1) and 2-bromo-1-(3-fluoro-phenyl)-ethanone was prepared 1'-({6-chloro-1-[2-(3-fluorophenyl)-2-oxoethyl]-1H-indol-3-yl}carbonyl)spiro[3,1-benzoxazine-4,4'-piperidin]-2(1H)-one.

ES-MS m/e (%): 532.4 (M+H⁺).

Example 13

1'-({6-Chloro-1-[2-(3,4-difluorophenyl)-2-oxoethyl]-1H-indol-3-yl}carbonyl)spiro[3,1-benzoxazine-4,4'-piperidin]-2(1H)-one

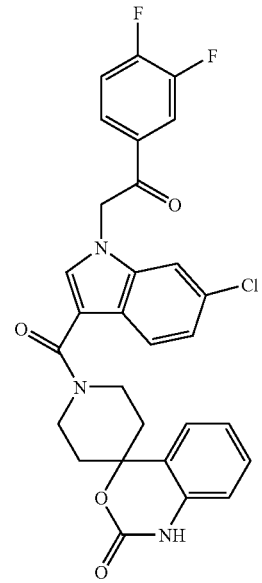

Using the same procedure described in example 6, from 1'-[(6-chloro-1H-indol-3-yl) carbonyl]spiro[3,1-benzoxazine-4,4'-piperidin]-2(1H)-one (described in example 1) and 2-bromo-1-(3,4-difluoro-phenyl)-ethanone was prepared 1'-({6-chloro-1-[2-(3,4-difluorophenyl)-2-oxoethyl]-1H-indol-3-yl}carbonyl)spiro[3,1-benzoxazine-4,4'-piperidin]-2(1H)-one.

ES-MS m/e (%): 550.4 (M+H⁺).

Example 14

1'-{[1-(Biphenyl-3-ylcarbonyl)-6-chloro-1H-indol-3-yl]carbonyl}spiro[3,1-benzoxazine-4,4'-piperidin]-2(1H)-one

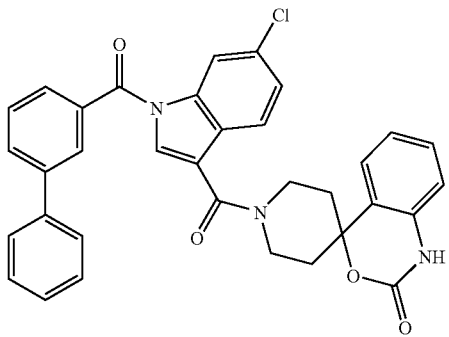

Using the same procedure described in example 6, from 1'-[(6-chloro-1H-indol-3-yl) carbonyl]spiro[3,1-benzoxazine-4,4'-piperidin]-2(1H)-one (described in example 1)

and biphenyl-3-carbonyl chloride was prepared 1'-{[1-(biphenyl-3-ylcarbonyl)-6-chloro-1H-indol-3-yl]carbonyl}spiro[3,1-benzoxazine-4,4'-piperidin]-2(1H)-one.
ES-MS m/e (%): 576.4 (M+H$^+$).

Example 15

1'-{[6-Chloro-1-(2-oxo-2-piperidin-1-ylethyl)-1H-indol-3-yl]carbonyl}spiro[3,1-benzoxazine-4,4'-piperidin]-2(1H)-one

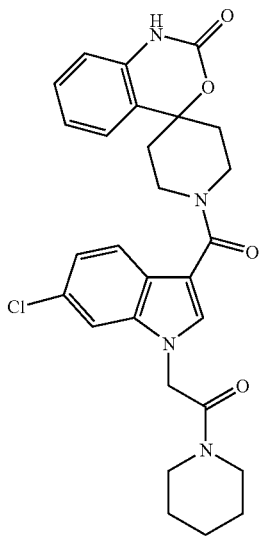

Using the same procedure described in example 6, from 1'-[(6-chloro-1H-indol-3-yl) carbonyl]spiro[3,1-benzoxazine-4,4'-piperidin]-2(1H)-one (described in example 1) and 2-chloro-1-piperidin-1-yl-ethanone was prepared 1'-{[6-chloro-1-(2-oxo-2-piperidin-1-ylethyl)-1H-indol-3-yl]carbonyl}spiro[3,1-benzoxazine-4,4'-piperidin]-2(1H)-one.
ES-MS m/e (%): 521.1 (M+H$^+$).

Example 16

1'-{[6-Chloro-1-(2-morpholin-4-yl-2-oxoethyl)-1H-indol-3-yl]carbonyl}spiro[3,1-benzoxazine-4,4'-piperidin]-2(1H)-one

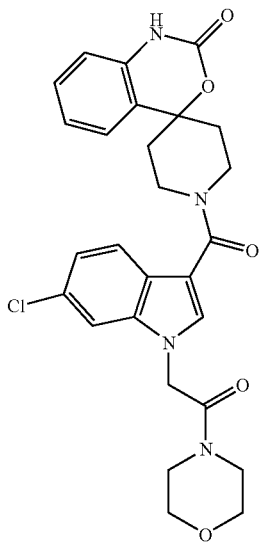

Using the same procedure described in example 6, from 1'-[(6-chloro-1H-indol-3-yl) carbonyl]spiro[3,1-benzoxazine-4,4'-piperidin]-2(1H)-one (described in example 1) and 2-chloro-1-morpholin-4-yl-2-oxoethyl)-1H-indol-3-yl]carbonyl}spiro[3,1-benzoxazine-4,4'-piperidin]-2(1H)-one.
ES-MS m/e (%): 523.2 (M+H$^+$).

Example 17

2-{6-Chloro-3-[(2-oxo-1,2-dihydro-1'H-spiro[3,1-benzoxazine-4,4'-piperidin]-1'-yl)carbonyl]-1H-indol-1-yl}-N,N-dimethylacetamide

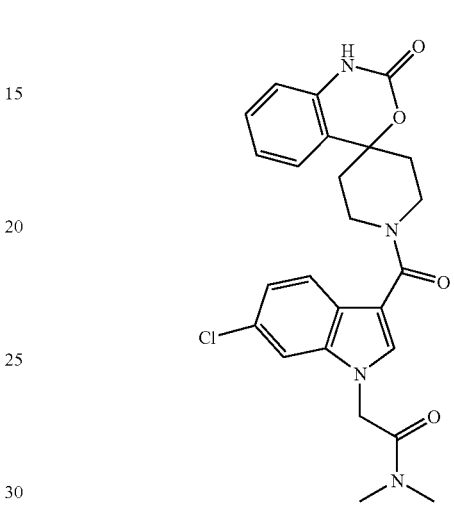

Using the same procedure described in example 6, from 1'-[(6-chloro-1H-indol-3-yl) carbonyl]spiro[3,1-benzoxazine-4,4'-piperidin]-2(1H)-one (described in example 1) and 2-chloro-N,N-dimethyl-acetamide was prepared 2-{6-chloro-3-[(2-oxo-1,2-dihydro-1H-spiro[3,1-benzoxazine-4,4'-piperidin]-1'-yl)carbonyl]-1H-indol-1-yl}-N,N-dimethylacetamide.
ES-MS m/e (%): 481.0 (M+H$^+$).

Example 18

2-{6-Chloro-3-[(2-oxo-1,2-dihydro-1H-spiro[3,1-benzoxazine-4,4'-piperidin]-1'-yl)carbonyl]-1H-indol-1-yl}-N,N-diethylacetamide

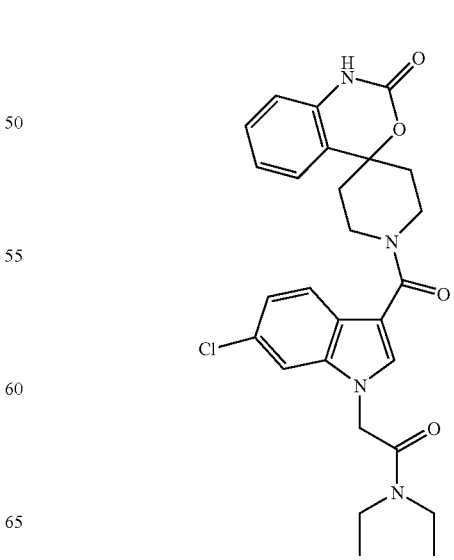

Using the same procedure described in example 6, from 1'-[(6-chloro-1H-indol-3-yl) carbonyl]spiro[3,1-benzoxazine-4,4'-piperidin]-2(1H)-one (described in example 1) and 2-chloro-N,N-diethyl-acetamide was prepared 2-{6-chloro-3-[(2-oxo-1,2-dihydro-1'H-spiro[3,1-benzoxazine-4,4'-piperidin]-1'-yl)carbonyl]-1H-indol-1-yl}-N,N-diethylacetamide.

ES-MS m/e (%): 509.1 (M+H⁺).

Example 19

1'-{[6-Chloro-1-(piperidin-1-ylcarbonyl)-1H-indol-3-yl]carbonyl}spiro[3,1-benzoxazine-4,4'-piperidin]-2(1H)-one

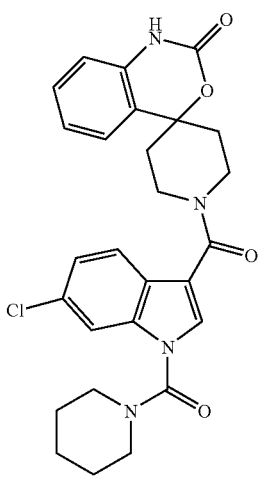

Using the same procedure described in example 6, from 1'-[(6-chloro-1H-indol-3-yl) carbonyl]spiro[3,1-benzoxazine-4,4'-piperidin]-2(1H)-one (described in example 1) and piperidine-1-carbonyl chloride was prepared 1'-{[6-chloro-1-(piperidin-1-ylcarbonyl)-1H-indol-3-yl]carbonyl}spiro[3,1-benzoxazine-4,4'-piperidin]-2(1H)-one.

ES-MS m/e (%): 507.1 (M+H⁺).

Example 20 tert-Butyl {6-chloro-3-[(2-oxo-1,2-dihydro-1'H-spiro[3,1-benzoxazine-4,4'-piperidin]-1'-yl)carbonyl]-1H-indol-1-yl}acetate

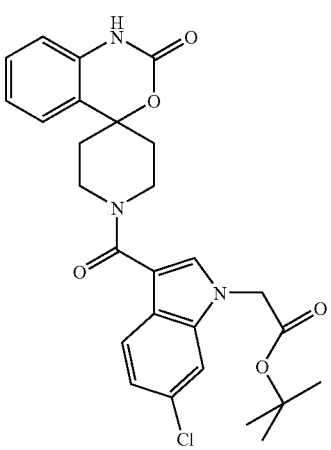

Using the same procedure described in example 6, from 1'-[(6-chloro-1H-indol-3-yl) carbonyl]spiro[3,1-benzox- azine-4,4'-piperidin]-2(1H)-one (described in example 1) and bromo-acetic acid tert-butyl ester was prepared tert-butyl {6-chloro-3-[(2-oxo-1,2-dihydro-1'H-spiro[3,1-benzoxazine-4,4'-piperidin]-1'-yl)carbonyl]-1H-indol-1-yl}acetate.

ES-MS m/e (%): 510.5 (M+H⁺).

Example 21

1'-{[6-Chloro-1-(3,5-difluorobenzoyl)-1H-indol-3-yl]carbonyl}spiro[3,1-benzoxazine-4,4'-piperidin]-2(1H)-one

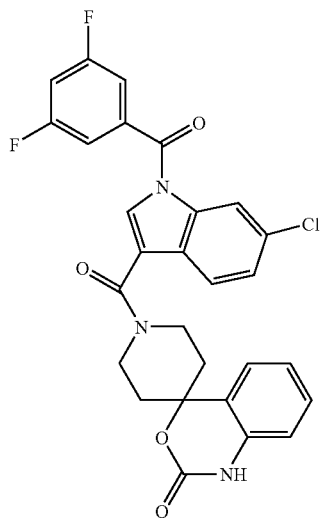

Using the same procedure described in example 6, from 1'-[(6-chloro-1H-indol-3-yl) carbonyl]spiro[3,1-benzoxazine-4,4'-piperidin]-2(1H)-one (described in example 1) and 3,5-difluoro-benzoyl chloride was prepared 1'-{[6-chloro-1-(3,5-difluorobenzoyl)-1H-indol-3-yl] carbonyl}spiro[3,1-benzoxazine-4,4'-piperidin]-2(1H)-one.

ES-MS m/e (%): 536.3 (M+H⁺).

Example 22

1'-({6-Chloro-1-[2-(3,5-difluorophenyl)-2-oxoethyl]-1H-indol-3-yl}carbonyl)spiro[3,1-benzoxazine-4,4'-piperidin]-2(1H)-one

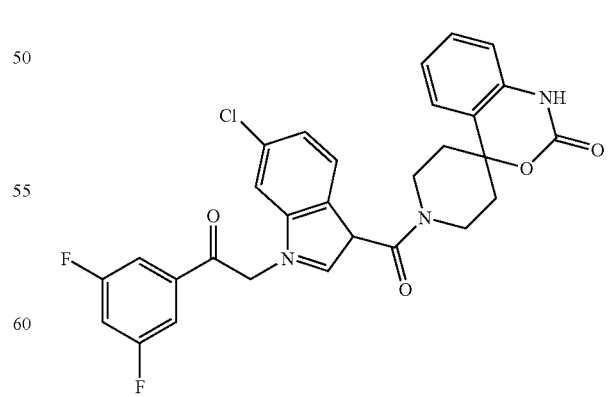

Using the same procedure described in example 6, from 1'-[(6-chloro-1H-indol-3-yl) carbonyl]spiro[3,1-benzoxazine-4,4'-piperidin]-2(1H)-one (described in example 1) and 2-bromo-1-(3,5-difluoro-phenyl)-ethanone was prepared 1'-({6-chloro-1-[2-(3,5-difluorophenyl)-2-oxoethyl]-1H-indol-3-yl}carbonyl)spiro[3,1-benzoxazine-4,4'-piperidin]-2(1H)-one.

ES-MS m/e (%): 550.3 (M+H⁺).

Example 23

1'-({6-Chloro-1-[2-(2-fluorophenyl)-2-oxoethyl]-1H-indol-3-yl}carbonyl)spiro[3,1-benzoxazine-4,4'-piperidin]-2(1H)-one

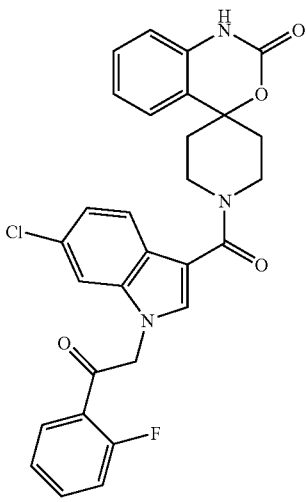

Using the same procedure described in example 6, from 1'-[(6-chloro-1H-indol-3-yl) carbonyl]spiro[3,1-benzoxazine-4,4'-piperidin]-2(1H)-one (described in example 1) and 2-bromo-1-(2-fluoro-phenyl)-ethanone was prepared 1'-({6-chloro-1-[2-(2-fluorophenyl)-2-oxoethyl]-1H-indol-3-yl}carbonyl)spiro[3,1-benzoxazine-4,4'-piperidin]-2(1H)-one.

ES-MS m/e (%): 532.3 (M+H⁺).

Example 24

3-{6-Chloro-3-[(2-oxo-1,2-dihydro-1'H-spiro[3,1-benzoxazine-4,4'-piperidin]-1'-yl)carbonyl]-1H-indol-1-yl}propanenitrile

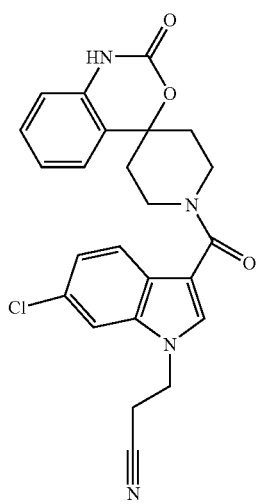

Using the same procedure described in example 6, from 1'-[(6-chloro-1H-indol-3-yl) carbonyl]spiro[3,1-benzoxazine-4,4'-piperidin]-2(1H)-one (described in example 1) and 3-cloro-propionitrile was prepared 3-{6-chloro-3-[(2-oxo-1,2-dihydro-1'H-spiro[3,1-benzoxazine-4,4'-piperidin]-1'-yl)carbonyl]-1H-indol-1-yl}propanenitrile.

ES-MS m/e (%): 449.0 (M+H⁺).

Example 25

2-{6-Chloro-3-[(2-oxo-1,2-dihydro-1'H-spiro[3,1-benzoxazine-4,4'-piperidin]-1'-yl)carbonyl]-1H-indol-1-yl}propanenitrile

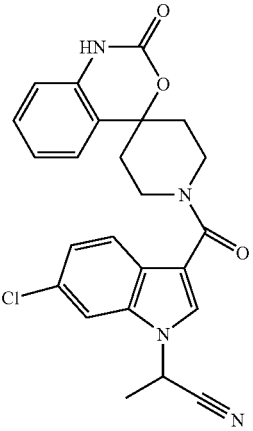

Using the same procedure described in example 6, from 1'-[(6-chloro-1H-indol-3-yl) carbonyl]spiro[3,1-benzoxazine-4,4'-piperidin]-2(1H)-one (described in example 1) and 2-chloro-propionitrile was prepared 2-{6-chloro-3-[(2-oxo-1,2-dihydro-1'H-spiro[3,1-benzoxazine-4,4'-piperidin]-1'-yl)carbonyl]-1H-indol-1-yl}propanenitrile.

ES-MS m/e (%): 449.0 (M+H⁺).

Example 26

1'-{[6-Chloro-1-(2-oxo-2-pyridin-2-ylethyl)-1H-indol-3-yl]carbonyl}spiro[3,1-benzoxazine-4,4'-piperidin]-2(1H)-one

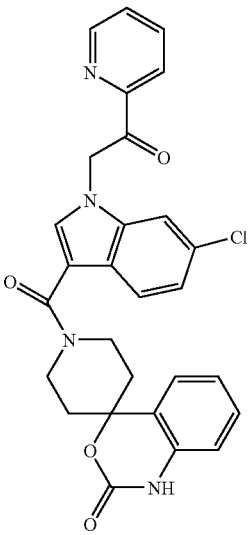

Using the same procedure described in example 6, from 1'-[(6-chloro-1H-indol-3-yl) carbonyl]spiro[3,1-benzoxazine-4,4'-piperidin]-2(1H)-one (described in example 1) and 2-bromo-1-pyridin-2-yl-ethanone was prepared 1'-{[6-chloro-1-(2-oxo-2-pyridin-2-ylethyl)-1H-indol-3-yl]carbonyl}spiro[3,1-benzoxazine-4,4'-piperidin]-2(1H)-one.

ES-MS m/e (%): 515.4 (M+H$^+$).

Example 27

1'-({6-Chloro-1-[2-(5-methyl-2-phenyl-1,3-oxazol-4-yl)-2-oxoethyl]-1H-indol-3-yl}carbonyl)spiro[3,1-benzoxazine-4,4'-piperidin]-2(1H)-one

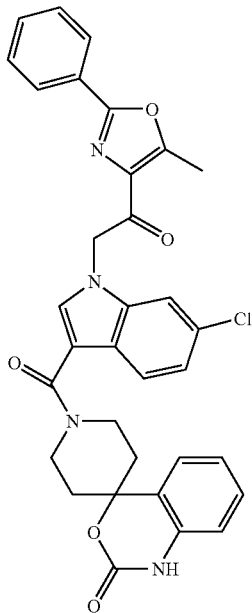

Using the same procedure described in example 6, from 1'-[(6-chloro-1H-indol-3-yl) carbonyl]spiro[3,1-benzoxazine-4,4'-piperidin]-2(1H)-one (described in example 1) and 2-bromo-1-(5-methyl-2-phenyl-oxazol-4-yl)-ethanone (described in J. Med. Chem. 1992, 35(14), 2617) was prepared 1'-({6-chloro-1-[2-(5-methyl-2-phenyl-1,3-oxazol-4-yl)-2-oxoethyl]-1H-indol-3-yl}carbonyl)spiro[3,1-benzoxazine-4,4'-piperidin]-2(1H)-one.

ES-MS m/e (%): 595.0 (M+H$^+$).

Example 28

2-{6-chloro-3-[(1-oxo-2,3-dihydro-1H, 1'H-spiro[isoquinoline-4,4'-piperidin]-1'-yl)carbonyl]-1H-indol-1-yl}-N-methylacetamide

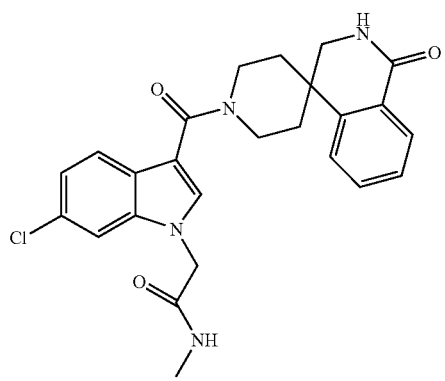

To a stirred solution of an 6-chloro-1-methylcarbamoyl-methyl-1H-indole-3-carboxylic acid (described below) (1 eq) in DMF were added HATU, (1.1 eq.), Et$_3$N (2 eq.) and (2 eq) of the 2,3-dihydro-1H-spiro[isoquinoline-4,4'-piperidin]-1-one (described previously in WO9909984). The mixture was stirred overnight at RT and then poured onto water and extracted with CH$_2$Cl$_2$. The combined organic phases were dried over Na$_2$SO$_4$ and concentrated in vacuo. Preparative HPLC afforded the title compound.

ES-MS m/e (%): 465.3 (M+H$^+$).

6-Chloro-1-methylcarbamoylmethyl-1H-indole-3-carboxylic acid a) 2-[6-Chloro-3-(2,2,2-trifluoro-acetyl)-indol-1-yl]-N-methyl-acetamide To a stirred solution of 1-(6-chloro-1H-indol-3-yl)-2,2,2-trifluoro-ethanone (described previously in U.S. 2004067939) in DMF were added 2.1 eq. NaH (60% in oil). The mixture was stirred at RT for 30 min. and then the (commercially available) 2-chloro-N-methyl-acetamide (1.1 eq.) was added. The mixture was stirred an additional 14 hours at 60° C. and then poured onto water and extracted with ethyl acetate. The combined organic phases were dried over Na$_2$SO$_4$ and concentrated in vacuo. Purification by preparative HPLC gave the title compound.

ES-MS m/e (%): 319.3 (M+H$^+$).

b) 6-Chloro-1-methylcarbamoylmethyl-1H-indole-3-carboxylic acid

2-[6-Chloro-3-(2,2,2-trifluoro-acetyl)-indol-1-yl]-N-methyl-acetamide was suspended in DCE and treated with (2.2 eq.) of sodium trimethylsilanolate. After shaking at room temperature for 20 min, the mixture was concentrated in vacuo and purified by prep. HPLC to give the title compound.

ES-MS m/e (%): 265.0 (M-H$^+$).

The invention claimed is:

1. A compound of formula (I)

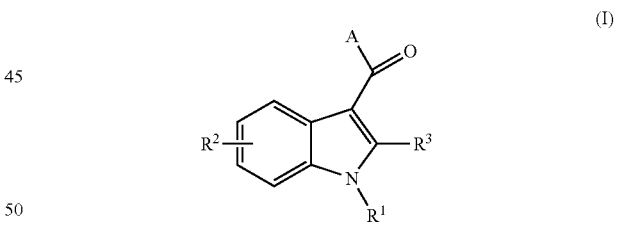

wherein

A is selected from the following groups (a), (b), (c), (d), (e) and (f):

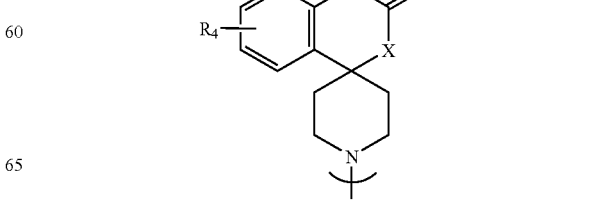

-continued (b)

(c)

(d)

(e)

(f)

each X is the same or different and is $CR^{iii}R^{iv}$, $NR^{iii}$ or O, wherein in (a), only one X can be O, the other being $CR^{iii}R^{iv}$ or $NR^{iii}$;

$R^1$ is H, $C_{1-6}$-alkyl optionally substituted by CN, aryl, 5 or 6 membered heteroaryl or sulfonylaryl each of which is optionally substituted by one or more B, —$(CH_2)_m$—$R^a$ wherein $R^a$ is:

$OR^i$, $NR^iR^{ii}$, or $C_{3-6}$-cycloalkyl, 4 to 7 membered-heterocycloalkyl, aryl, or 5 or 6 membered heteroaryl each of which is optionally substituted by one or more B, or —$(CH_2)_n$—(CO)—$R^b$ or —$(CH_2)_n$-($SO_2$)—$R^b$, wherein $R^b$ is:

$C_{1-6}$-alkyl,
$C_{1-6}$-alkoxy,
$C_{3-6}$-cycloalkyl,
—$(CH_2)_m$—$NR^{iii}R^{iv}$,
$NR^iR^{ii}$, or
$C_{3-6}$-cycloalkyl, 4 to 7 membered-heterocycloalkyl, aryl, or 5 or 6 membered heteroaryl each of which is optionally substituted by one or more B, or $R^1$ and $R^3$ together with the indole ring to which they are attached form a 5 or 6 membered heterocycloalkyl which can be substituted by (CO);

there can be one or more $R^2$ wherein each $R^2$ is H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, benzyloxy, or $C_{1-6}$-haloalkyl, or two $R^2$ together with the indole ring to which they are attached form an oxo or dioxo bridge;

$R^3$ is H,
halo,
—(CO)—$R^c$, wherein $R^c$ is:
$C_{1-6}$-alkyl,
—$(CH_2)_n$—$NR^iR^{ii}$,
—$(CH_2)_n$—$NR^{iii}R^{iv}$, or
5 or 6 membered heterocycloalkyl optionally substituted by $C_{1-6}$-alkyl, or $C_{1-6}$-alkyl or aryl, each of which is optionally substituted by
halo,
—O(CO)—$C_{1-6}$-alkyl,
or —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

there can be one or more $R^4$ wherein each
$R^4$ is H, halo, $C_{1-6}$ alkyl, $C_{1-6}$ alkoxy, or CN,
or two $R^4$ together with the phenyl ring to which they are attached form an oxo or dioxo bridge;

B is halo,
CN,
$C_{1-6}$-alkyl optionally substituted by CN, halo or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl,
—C(O) $NR^iR^{ii}$,
—C(O)—$C_{1-6}$-alkyl,
—$S(O)_2$—$C_{1-6}$-alkyl,
—$S(O)_2$—$NR^iR^{ii}$, or
$(CR^{iii}R^{iv})_n$-phenyl, or $(CR^{iii}R^{iv})_n$-5 or 6 membered heteroaryl wherein the phenyl or 5 or 6 membered heteroaryl moiety is optionally substituted by one or more substituent(s) selected from the group consisting of:
halo, CN, $NR^iR^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—$NR^iR^{ii}$, —C(O)—$C_{1-6}$-alkyl, —$S(O)_2$—$C_{1-6}$-alkyl, and —$S(O)_2$—$NR^iR^{ii}$;

$R^i$ and $R^{ii}$ are each independently H, $C_{1-6}$-alkyl, $C_{1-6}$-alkylene-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl or —$S(O)_2$—$NR^{iii}R^{iv}$;

$R^{iii}$ is H, $C_{1-6}$-alkyl or $C_{1-6}$-alkylene-$N(R^{iv})_2$;
$R^{iv}$ is H or $C_{1-6}$-alkyl;
m is 1 to 6; and
n is 0 to 4;
or a pharmaceutically acceptable salt thereof.

2. The compound of claim 1, wherein
there can be one or more $R^2$ wherein each
$R^2$ is H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, or benzyloxy,
or two $R^2$ together with the indole ring to which they are attached form an oxo or dioxo bridge; and
$R^{iii}$ and $R^{iv}$ are each independently H or $C_{1-6}$-alkyl.

3. The compound of claim 1 having formula (I-a):

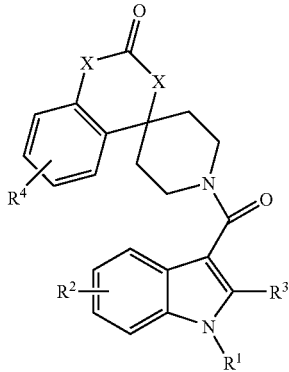

(I-a)

wherein:
each X is the same or different and is $CR^{iii}R^{iv}$, $NR^{iii}$ or O, wherein only one X can be O, the other being $CR^{iii}R^{iv}$ or $NR^{iii}$;
$R^1$ is H,
  $C_{1-6}$-alkyl optionally substituted by CN,
  aryl optionally substituted by one or more B,
  —$(CH_2)_m$—$R^a$ wherein $R^a$ is:
    $NR^iR^{ii}$, or
    aryl optionally substituted by one or more B,
  or —$(CH_2)_n$—(CO)—$R^b$ or —$(CH_2)_n$—$(SO_2)$—$R^b$, wherein $R^b$ is:
    $C_{1-6}$-alkoxy,
    $NR^iR^{ii}$, or
    4 to 7 membered-heterocycloalkyl, aryl, or 5 or 6 membered heteroaryl each of which is optionally substituted by one or more B,
there can be one or more $R^2$ wherein each
$R^2$ is H or halo,
$R^3$ is H or $C_{1-6}$-alkyl,
there can be one or more $R^4$ wherein each
$R^4$ is H, halo, $C_{1-6}$ alkyl, $C_{1-6}$ alkoxy or CN;
B is halo,
  CN,
  $NR^iR^{ii}$,
  $C_{1-6}$-alkyl optionally substituted by CN, halo or $C_{1-6}$-alkoxy,
  $C_{1-6}$-alkoxy,
  $C_{1-6}$-haloalkoxy,
  $C_{3-6}$-cycloalkyl,
  —C(O)O—$C_{1-6}$-alkyl,
  —C(O) $NR^iR^{ii}$,
  —C(O)—$C_{1-6}$-alkyl,
  —$S(O)_2$—$C_{1-6}$-alkyl,
  —$S(O)_2$—$NR^iR^{ii}$, or
  $(CR^{iii}R^{iv})$n-phenyl, or $(CR^{iii}R^{iv})$n-5 or 6 membered heteroaryl wherein the phenyl or 5 or 6 membered heteroaryl moiety is optionally substituted by one or more substituent(s) selected from the group consisting of:
    halo, CN, $NR^iR^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—$NR^iR^{ii}$, —C(O)—$C_{1-6}$-alkyl, —$S(O)_2$—$C_{1-6}$-alkyl, and —$S(O)_2$—$NR^iR^{ii}$;
$R^i$ and $R^{ii}$ are each independently H, $C_{1-6}$-alkyl, $C_{1-6}$-alkylene-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl or —$S(O)_2$—$NR^{iii}R^{iv}$;
$R^{ii}$ is H, $C_{1-6}$-alkyl or $C_{1-6}$-alkylene-$N(R^{iv})_2$;
$R^{iv}$ is H or $C_{1-6}$-alkyl;
m is 1 to 6; and
n is 0 to 4;
or a pharmaceutically acceptable salt thereof.

4. The compound of claim 3, wherein $R^{iii}$ and $R^{iv}$ are each independently H or $C_{1-6}$-alkyl.

5. The compound of claim 3, wherein group (a) of the compound of formula (I-a) is selected from (a') and (a"):

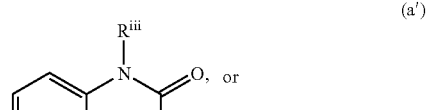

(a')

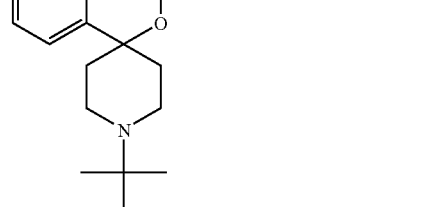

(a")

wherein $R^{iii}$ is H, $C_{1-6}$-alkyl or $C_{1-6}$-alkylene-$N(R^{iv})_2$ and $R^{iv}$ is H or $C_{1-6}$-alkyl.

6. The compound of claim 3, wherein $R^1$ is H.

7. The compound of claim 6, selected from the group consisting of:
1'-[(6-Chloro-1H-indol-3-yl)carbonyl]spiro[3,1-benzoxazine-4,4'-piperidin]-2(1H)-one;
6'-Bromo-1-(1H-indol-3-ylcarbonyl)-1'H-spiro[piperidine-4,4'-quinolin]-2'(3'H)-one;
6-Chloro-1'-[(6-chloro-1H-indol-3-yl)carbonyl]-1-[2-(dimethylamino)ethyl]spiro[3,1-benzoxazine-4,4'-piperidin]-2 (1H)-one; and
6-Chloro-1'-[(6-chloro-1H-indol-3-yl)carbonyl]spiro[3,1-benzoxazine-4,4'-piperidin]-2(1H)-one.

8. The compound of claim 3, wherein $R^1$ is aryl optionally substituted by one or more B.

9. The compound of claim 8, which is 1'-{[6-chloro-1-(3,5-difluorophenyl)-1H-indol-3-yl]carbonyl}spiro[3,1-benzoxazine-4,4'-piperidin]-2(1H)-one.

10. The compound of claim 3, wherein $R^1$ is C1-6 alkyl optionally substituted by CN or —$(CH_2)_m$-$R^a$ and wherein $R^a$ is CN, $NR^iR^{ii}$, or aryl optionally substituted by one or more B.

11. The compound of claim 10, selected from the group consisting of:
1'-{[6-Chloro-1-(3,5-difluorobenzyl)-1H-indol-3-yl]carbonyl}spiro[3,1-benzoxazine-4,4'-piperidin]-2(1H)-one;
1'-{[6-Chloro-1-(3-fluorobenzyl)-1H-indol-3-yl]carbonyl}spiro[3,1-benzoxazine-4,4'-piperidin]-2(1H)-one;
3-{6-Chloro-3-[(2-oxo-1,2-dihydro-1'H-spiro[3,1-benzoxazine-4,4'-piperidin]-1'-yl)carbonyl]-1H-indol-1-yl}propanenitrile; and
2-{6-Chloro-3-[(2-oxo-1,2-dihydro-1'H-spiro[3,1-benzoxazine-4,4'-piperidin]-1'-yl)carbonyl]-1H-indol-1-yl}propanenitrile.

12. The compound of claim 3, wherein $R^1$ is —$(CH^2)_n$-(CO)—$R^b$ or —$(CH_2)_n$—$(SO_2)$—$R^b$, wherein $R^b$ is $C_{1-6}$-alkoxy, $NR^iR^{ii}$, or is 4 to 7 membered-heterocycloalkyl, aryl, or 5 or 6 membered heteroaryl each of which is optionally substituted by one or more B.

13. The compound of claim 12, selected from the group consisting of:
1'-{[6-Chloro-1-(3-fluorobenzoyl)-1H-indol-3-yl]carbonyl}spiro[3,1-benzoxazine-4,4'-piperidin]-2(1H)-one;
1'-{[6-Chloro-1-(2-fluorobenzoyl)-1H-indol-3-yl]carbonyl}spiro[3,1-benzoxazine-4,4'-piperidin]-2(1H)-one;
1'-{[6-Chloro-1-(2,3-difluorobenzoyl)-1H-indol-3-yl]carbonyl}spiro[3,1-benzoxazine-4,4'-piperidin]-2(1H)-one;
1'-({6-Chloro-1-[(3,5-difluorophenyl)sulfonyl]-1H-indol-3-yl}carbonyl)spiro[3,1-benzoxazine-4,4'-piperidin]-2(1H)-one;
1'-({6-Chloro-1-[2-(3-fluorophenyl)-2-oxoethyl]-1H-indol-3-yl}carbonyl)spiro[3,1-benzoxazine-4,4'-piperidin]-2(1H)-one;
1'-({6-Chloro-1-[2-(3,4-difluorophenyl)-2-oxoethyl]-1H-indol-3-yl}carbonyl)spiro[3,1-benzoxazine-4,4'-piperidin]-2(1H)-one;
1'-{[1-(Biphenyl-3-ylcarbonyl)-6-chloro-1H-indol-3-yl]carbonyl}spiro[3,1-benzoxazine-4,4'-piperidin]-2(1H)-one;
1'-{[6-Chloro-1-(2-oxo-2-piperidin-1-ylethyl)-1H-indol-3-yl]carbonyl}spiro[3,1-benzoxazine-4,4'-piperidin]-2(1H)-one;
1'-{[6-Chloro-1-(2-morpholin-4-yl-2-oxoethyl)-1H-indol-3-yl]carbonyl}spiro[3,1-benzoxazine-4,4'-piperidin]-2(1H)-one; and
2-{6-Chloro-3-[(2-oxo-1,2-dihydro-1'H-spiro[3,1-benzoxazine-4,4'-piperidin]-1'-yl)carbonyl]-1H-indol-1-yl}-N,N-dimethylacetamide.

14. The compound of claim 12, selected from the group consisting of:
2-{6-Chloro-3-[(2-oxo-1,2-dihydro-1'H-spiro[3,1-benzoxazine-4,4'-piperidin]-1'-yl)carbonyl]-1H-indol-1-yl}-N,N-diethylacetamide;
1'-{[6-Chloro-1-(piperidin-1-ylcarbonyl)-1H-indol-3-yl]carbonyl}spiro[3,1-benzoxazine-4,4'-piperidin]-2(1H)-one;
tert-Butyl {6-chloro-3-[(2-oxo-1,2-dihydro-1'H-spiro[3,1-benzoxazine-4,4'-piperidin]-1'-yl)carbonyl]-1H-indol-1-yl}acetate;
1'-{[6-Chloro-1-(3,5-difluorobenzoyl)-1H-indol-3-yl]carbonyl}spiro[3,1-benzoxazine-4,4'-piperidin]-2(1H)-one;
1'-({6-Chloro-1-[2-(3,5-difluorophenyl)-2-oxoethyl]-1H-indol-3-yl}carbonyl)spiro[3,1-benzoxazine-4,4'-piperidin]-2(1H)-one;
1'-({6-Chloro-1-[2-(2-fluorophenyl)-2-oxoethyl]-1H-indol-3-yl}carbonyl)spiro[3,1-benzoxazine-4,4'-piperidin]-2(1H)-one;
1'-{[6-Chloro-1-(2-oxo-2-pyridin-2-ylethyl)-1H-indol-3-yl]carbonyl}spiro[3,1-benzoxazine-4,4'-piperidin]-2(1H)-one; and
1'-({6-Chloro-1-[2-(5-methyl-2-phenyl-1,3-oxazol-4-yl)-2-oxoethyl]-1H-indol-3-yl}carbonyl)spiro[3,1-benzoxazine-4,4'-piperidin]-2(1H)-one.

15. The compound of claim 1, having formula (I-b):

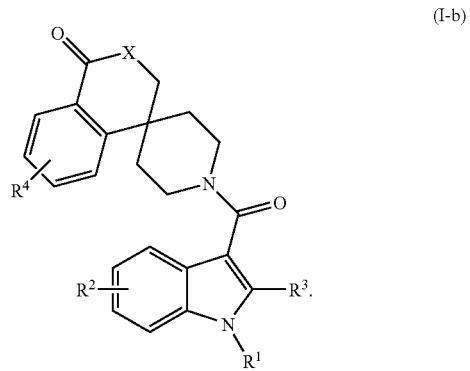

16. The compound of claim 15, which is 2-{6-chloro-3-[(1-oxo-2,3-dihydro-1H,1'H-spiro[isoquinoline-4,4'-piperidin]-1'-yl)carbonyl]-1H-indol-1-yl}-N-methylacetamide.

17. The compound of claim 1, having formula (I-c):

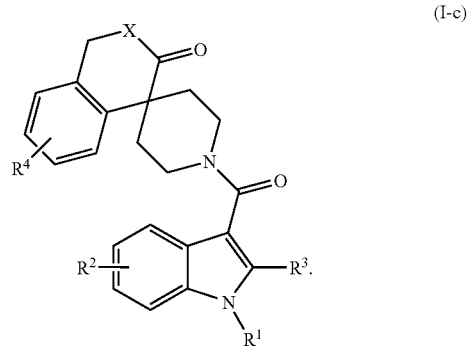

18. The compound of claim 1, having formula (I-d):

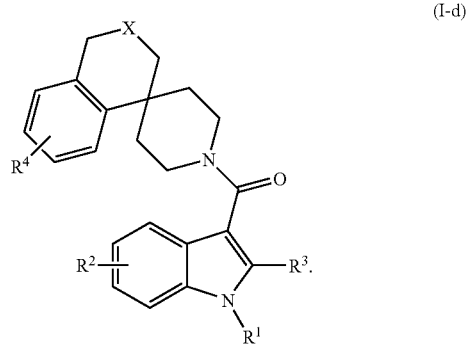

19. The compound of claim 1, having formula (I-e):

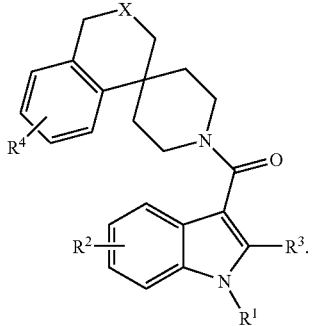
(I-e)

20. The compound of claim 1, having formula (I-f):

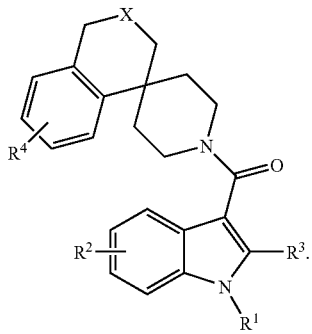
(I-f)

21. A pharmaceutical composition comprising a compound of formula (I)

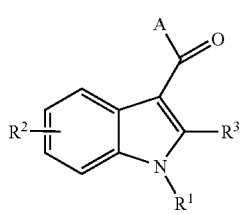
(I)

wherein

A is selected from the following groups (a), (b), (c), (d), (e) and (f):

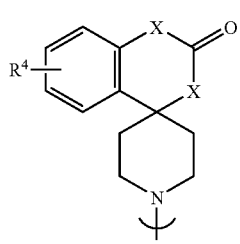
(a)

-continued

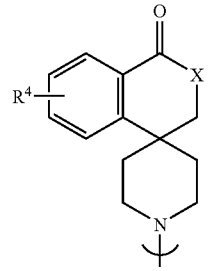
(b)

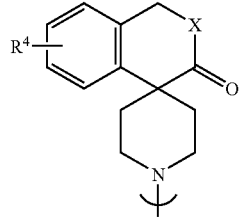
(c)

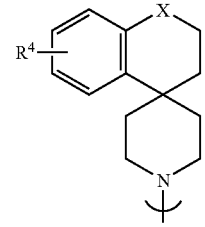
(d)

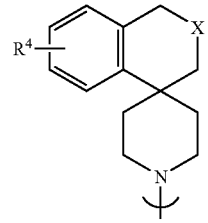
(e)

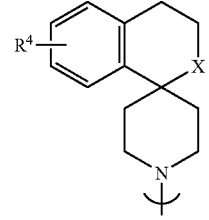
(f)

each X is the same or different and is $CR^{iii}R^{iv}$, $NR^{iii}$ or O, wherein in (a), only one X can be O, the other being $CR^{iii}R^{iv}$ or $NR^{iii}$;

$R^1$ is H, $C_{1-6}$-alkyl optionally substituted by CN, aryl, 5 or 6 membered heteroaryl or sulfonylaryl each of which is optionally substituted by one or more B, —$(CH_2)_m$—$R^a$ wherein $R^a$ is:

$OR^i$, $NR^iR^{ii}$, or $C_{3-6}$-cycloalkyl, 4 to 7 membered-heterocycloalkyl, aryl, or 5 or 6 membered heteroaryl each of which is optionally substituted by one or more B, or —$(CH_2)_n$—$(CO)$—$R^b$ or —$(CH_2)_n$-$(SO_2)$—$R^b$, wherein R is:

$C_{1-6}$-alkyl,
$C_{1-6}$-alkoxy,
$C_{3-6}$-cycloalkyl,
—$(CH_2)_m$—$NR^{iii}R^{iv}$,
$NR^iR^{ii}$, or
$C_{3-6}$-cycloalkyl, 4 to 7 membered-heterocycloalkyl, aryl, or 5 or 6 membered heteroaryl each of which is optionally substituted by one or more B, or $R^1$ and $R^3$ together with the indole ring to which they are attached form a 5 or 6 membered heterocycloalkyl which can be substituted by (CO);

there can be one or more $R^2$ wherein each
$R^2$ is H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, benzyloxy, or $C_{1-6}$-haloalkyl, or two $R^2$ together with the indole ring to which they are attached form an oxo or dioxo bridge;

$R^3$ is H,
halo,
—(CO)—$R^c$, wherein $R^c$ is:
$C_{1-6}$-alkyl,
—$(CH_2)_n$—$NR^iR^{ii}$,
—$(CH_2)_n$—$NR^{iii}R^{iv}$, or
5 or 6 membered heterocycloalkyl optionally substituted by $C_{1-6}$-alkyl, or $C_{1-6}$-alkyl or aryl, each of which is optionally substituted by halo,
—O(CO)—$C_{1-6}$-alkyl,
or —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

there can be one or more $R^4$ wherein each
$R^4$ H, halo, $C_{1-6}$ alkyl, $C_{1-6}$ alkoxy, or CN, or two $R^4$ together with the phenyl ring to which they are attached form an oxo or dioxo bridge;

B is halo,
CN,
$NR^iR^{ii}$,
$C_{1-6}$-alkyl optionally substituted by CN, halo or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl,
—C(O) $NR^iR^{ii}$,
—C(O)—$C_{1-6}$-alkyl,
—S(O)$_2$—$C_{1-6}$-alkyl,
—S(O)$_2$—$NR^iR^{ii}$, or
$(CR^{iii}R^{iv})_n$-phenyl, or $(CR^{iii}R^{iv})_n$-5 or 6 membered heteroaryl wherein the phenyl or 5 or 6 membered heteroaryl moiety is optionally substituted by one or more substituent(s) selected from the group consisting of:
halo, CN, $NR^iR^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—$NR^iR^{ii}$, —C(O)—$C_{1-6}$-alkyl, —S(O)$_2$—$C_{1-6}$-alkyl, and —S(O)$_2$—$NR^iR^{ii}$;

$R^i$ and $R^{ii}$ are each independently H, $C_{1-6}$-alkyl, $C_{1-6}$-alkylene-$NR^{iii}R^{iv}$, —(CO)O—$C_{1-6}$-alkyl, —C(O)—$NR^{iii}R^{iv}$, —C(O)—$C_{1-6}$-alkyl, —S(O)$_2$—$C_{1-6}$-alkyl or —S(O)$_2$—$NR^{iii}R^{iv}$;

$R^{iii}$ is H, $C_{1-6}$-alkyl or $C_{1-6}$-alkylene—$N(R^{iv})_2$;

$R^{iv}$ is H or $C_{1-6}$-alkyl;

m is 1 to 6; and n is 0 to 4;

or a pharmaceutically acceptable salt thereof and a pharmaceutically acceptable carrier.

* * * * *